(12) United States Patent
Windus-Smith et al.

(10) Patent No.: US 7,617,932 B2
(45) Date of Patent: *Nov. 17, 2009

(54) MEDICAL DEVICE PACKAGE, KIT AND ASSOCIATED METHODS

(75) Inventors: Bryan Windus-Smith, Moray (GB); John Allen, Mendota Heights, MN (US)

(73) Assignee: Diabetes Diagnostics, Inc., Waltham, MA (US)

( * ) Notice: Subject to any disclaimer, the term of this patent is extended or adjusted under 35 U.S.C. 154(b) by 442 days.

This patent is subject to a terminal disclaimer.

(21) Appl. No.: 10/666,154

(22) Filed: Sep. 19, 2003

(65) Prior Publication Data

US 2005/0061700 A1 Mar. 24, 2005

(51) Int. Cl.
*B65D 85/00* (2006.01)
*A61B 19/02* (2006.01)

(52) U.S. Cl. .................................. 206/363; 206/438
(58) Field of Classification Search ............... 206/355, 206/359, 356, 352, 367, 363, 438, 569, 305, 206/365; 606/167; 30/339; 600/583
See application file for complete search history.

(56) References Cited

U.S. PATENT DOCUMENTS

| | | | |
|---|---|---|---|
| 4,106,620 A | 8/1978 | Brimmer et al. | |
| 4,180,162 A | 12/1979 | Magney | |
| 4,746,016 A * | 5/1988 | Pollak et al. | 206/356 |
| 4,903,390 A * | 2/1990 | Vidal et al. | 29/239 |
| 4,985,034 A | 1/1991 | Lipton | |
| 5,035,703 A | 7/1991 | Baskas | |
| 5,432,214 A | 7/1995 | Lancesseur | |
| 5,528,811 A * | 6/1996 | Abidin et al. | 29/428 |
| 5,656,502 A | 8/1997 | MacKay et al. | |

(Continued)

FOREIGN PATENT DOCUMENTS

EP 0824480 B1 1/2001

(Continued)

OTHER PUBLICATIONS

Mexican Official Letter, Aug. 6, 2007, Mexico D.F., Mexico, re Mexican Patent Application PA/A/2004/009128.

*Primary Examiner*—Mickey Yu
*Assistant Examiner*—Steven A. Reynolds
(74) *Attorney, Agent, or Firm*—Wayne Jaeschke, Jr.

(57) ABSTRACT

A medical device package for receiving, and securely and removably retaining, a medical device includes main and minor cap members. The main cap member has a proximal end, a distal end and a cavity with a cavity opening at the proximal end. The cavity is configured to receive, and to securely and removably retain, the medical device at least partially therein. The minor cap member is configured to seal the cavity opening once the medical device has been received in the cavity. Kits further include a connector adapted for engaging the medical device member and breaching the minor cap member. A method for extracting a medical device from a medical device package includes first providing a medical device package as described above, with a medical device therein, and a connector. The method also includes breaching the minor cap member with the connector such that at least a portion of the connector enters the cavity of the medical device package. Next, the medical device is engaged by the connector and extracted from the medical device package.

6 Claims, 28 Drawing Sheets

U.S. PATENT DOCUMENTS

| | | | |
|---|---|---|---|
| 5,938,027 A * | 8/1999 | Soroff et al. | 206/370 |
| 6,116,440 A | 9/2000 | Zaksenberg et al. | |
| 6,176,119 B1 | 1/2001 | Kintzig | |
| 6,183,467 B1 | 2/2001 | Shapeton et al. | |
| 6,216,868 B1 * | 4/2001 | Rastegar et al. | 206/359 |
| 6,217,701 B1 | 4/2001 | Shelley et al. | |
| 6,247,604 B1 | 6/2001 | Taskis et al. | |
| 6,273,941 B1 | 8/2001 | Law | |
| 6,324,896 B1 | 12/2001 | Aoyagi et al. | |
| 6,378,702 B1 | 4/2002 | Kintzig | |
| 6,497,845 B1 | 12/2002 | Sacherer | |
| 6,531,197 B2 | 3/2003 | Neteler | |
| 6,534,017 B1 | 3/2003 | Bottwein et al. | |
| 6,682,704 B2 | 1/2004 | Bottwein et al. | |
| 6,706,154 B1 | 3/2004 | Yang et al. | |
| 2002/0006483 A1 | 1/2002 | Neteler | |
| 2002/0014305 A1 | 2/2002 | Dick et al. | |
| 2002/0143352 A1 * | 10/2002 | Newman et al. | 606/167 |
| 2002/0168290 A1 * | 11/2002 | Yuzhakov et al. | 422/56 |
| 2002/0177763 A1 | 11/2002 | Burns et al. | |
| 2003/0036200 A1 | 2/2003 | Charlton | |
| 2003/0143113 A2 | 7/2003 | Yuzhakov et al. | |
| 2003/0144608 A1 * | 7/2003 | Kojima et al. | 600/583 |
| 2004/0156747 A1 | 8/2004 | Jochumsen et al. | |

FOREIGN PATENT DOCUMENTS

| | | |
|---|---|---|
| EP | 1 118 856 A1 | 7/2001 |
| EP | 1118552 A2 | 7/2001 |
| EP | 1 285 695 A2 | 2/2003 |
| EP | 1288251 A2 | 3/2003 |
| WO | WO 96/02290 A | 2/1996 |
| WO | WO 97/10014 A | 3/1997 |
| WO | WO 99/62697 A1 | 12/1999 |
| WO | WO 00/13986 A1 | 3/2000 |
| WO | WO 01/26782 A1 | 4/2001 |
| WO | WO 01/64105 A1 | 9/2001 |
| WO | WO 01/87731 A2 | 11/2001 |
| WO | WO 02/43507 | 6/2002 |
| WO | WO 02/49507 A1 | 6/2002 |
| WO | WO 03/015627 A2 | 2/2003 |

* cited by examiner

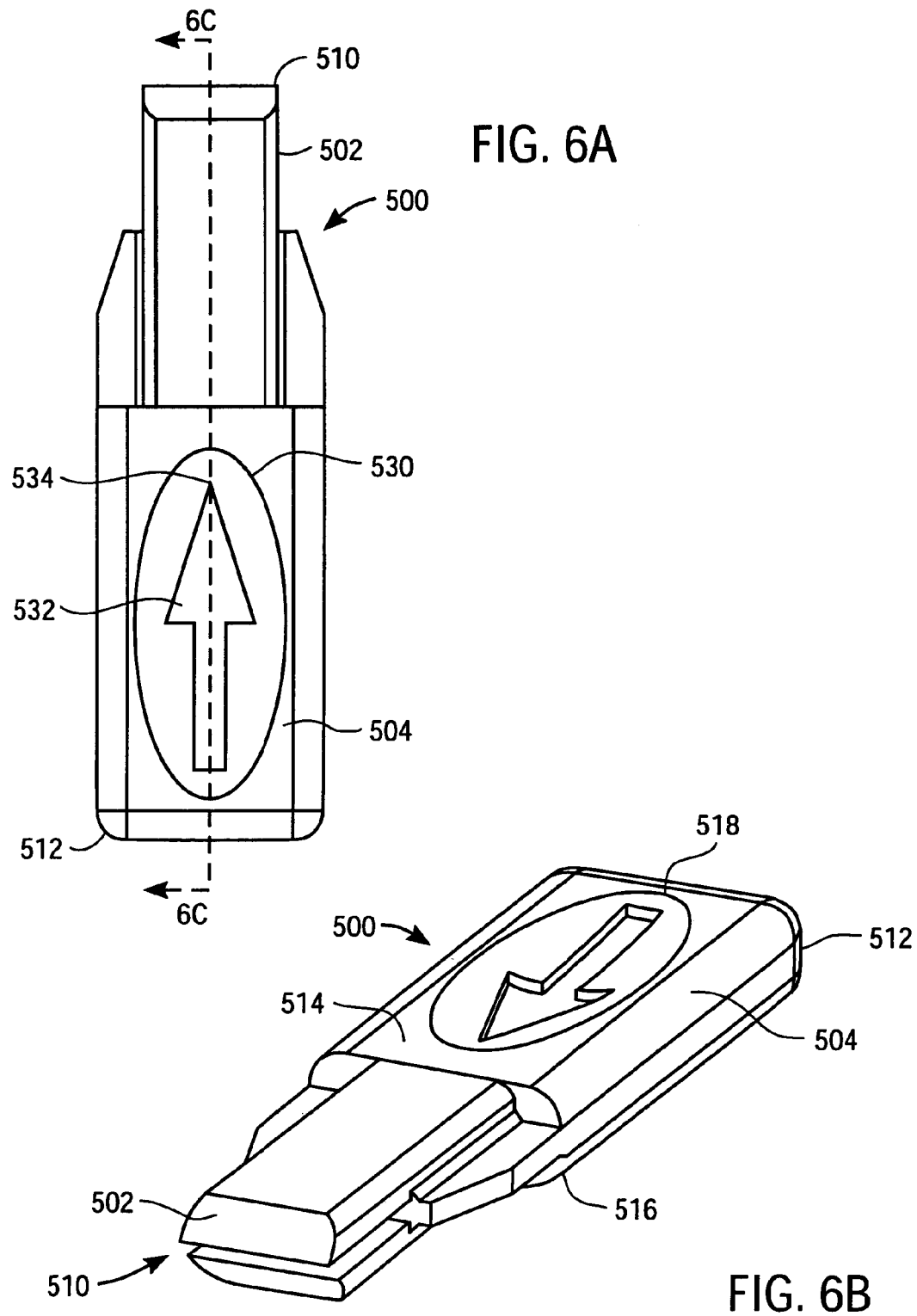

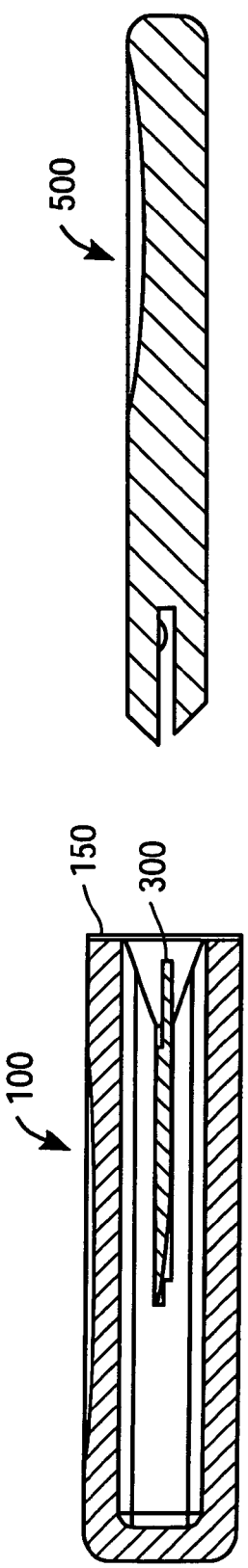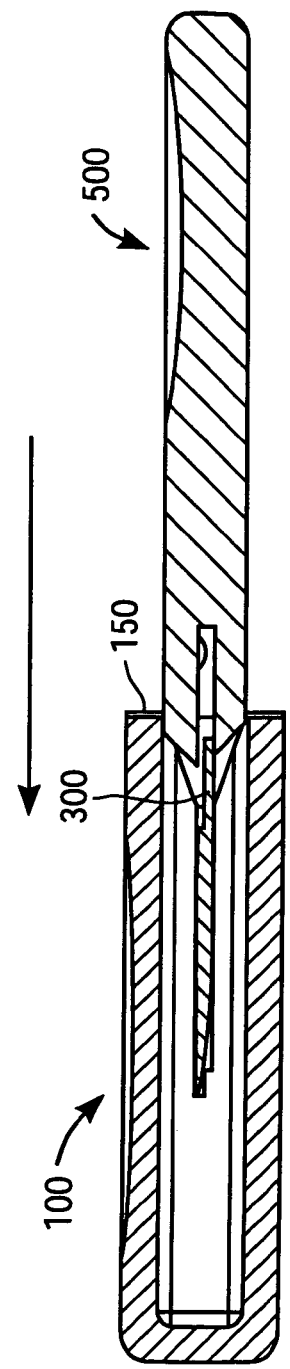
FIG. 9A
FIG. 9B

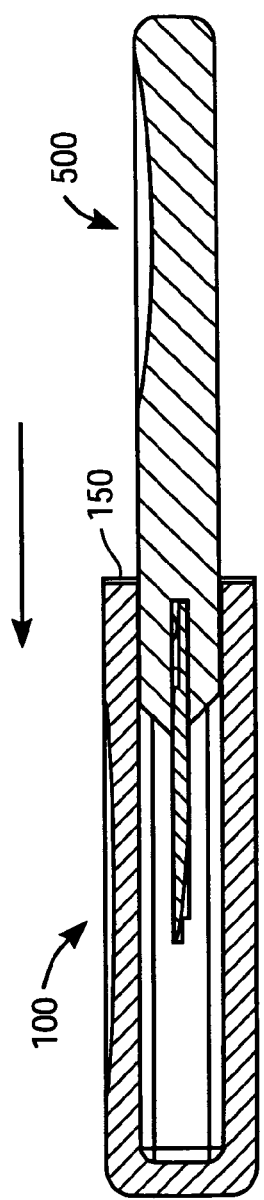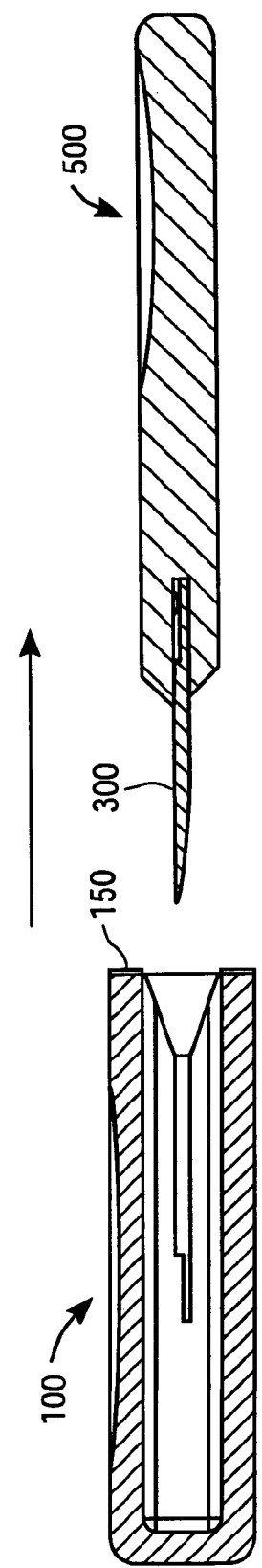
FIG. 9C
FIG. 9D

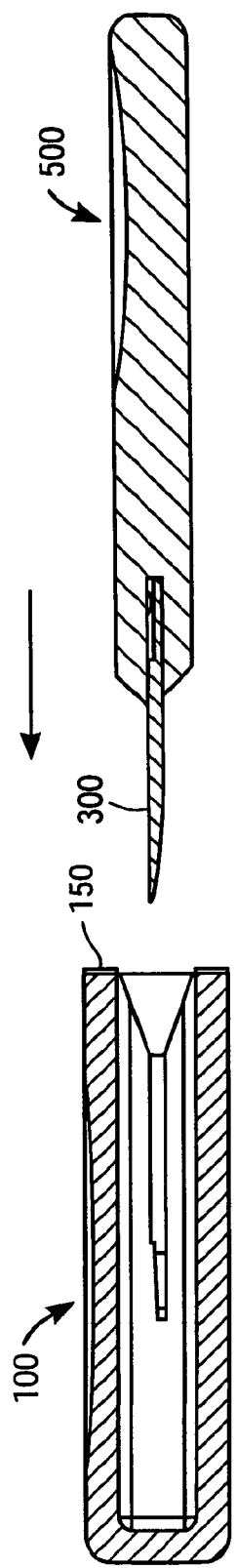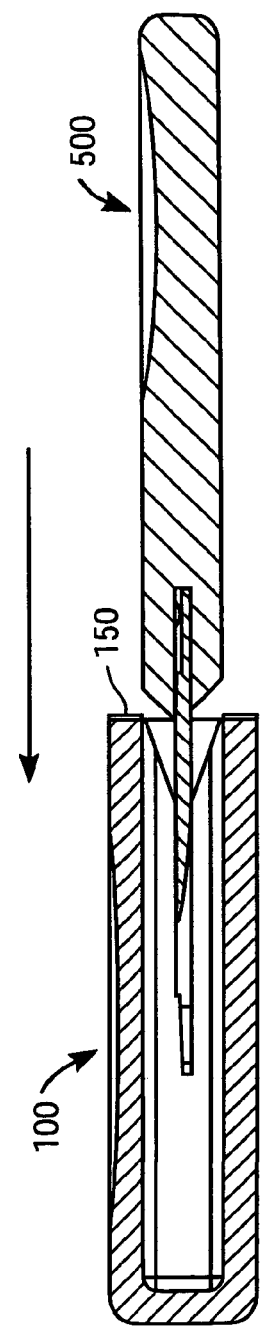
FIG. 14A
FIG. 14B

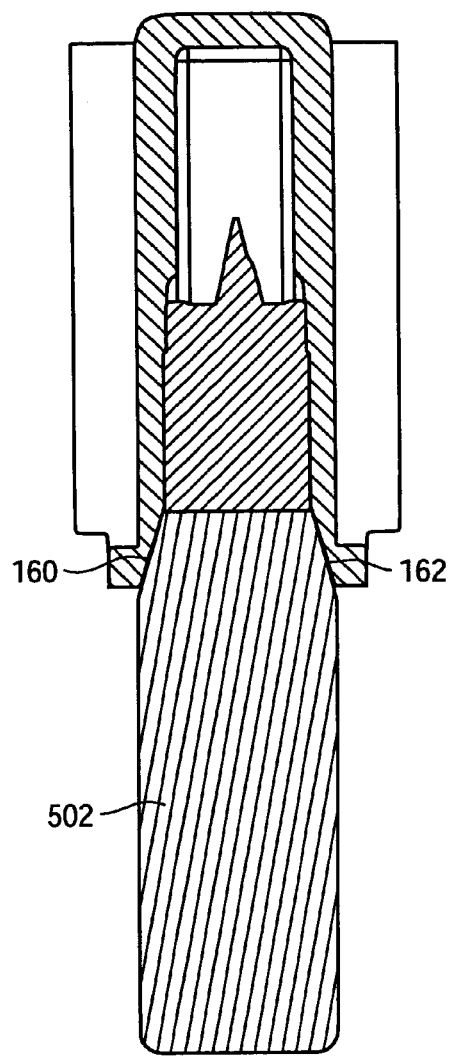
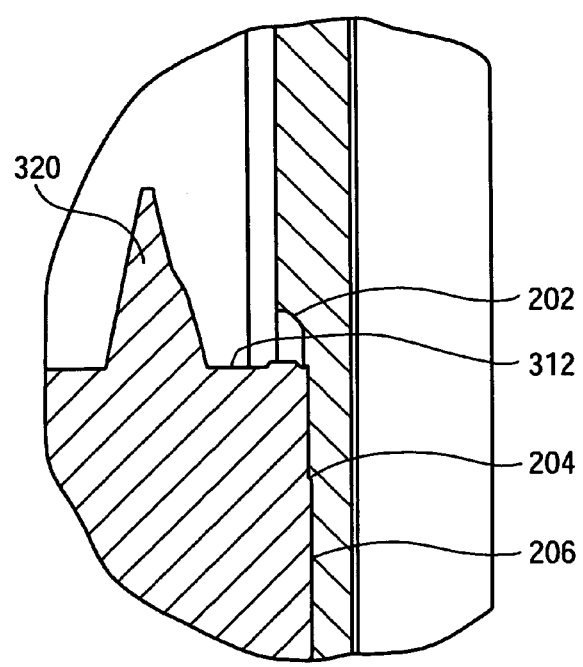
FIG. 16A
FIG. 16B

MEDICAL DEVICE PACKAGE, KIT AND ASSOCIATED METHODS

BACKGROUND OF THE INVENTION

1. Field of the Invention

The present invention relates, in general, to medical device packages and, in particular, to medical device packages for receiving, and securely and removably retaining, a medical device.

2. Description of the Related Art

A variety of medical devices require packaging to, for example, protect the medical device from damage prior to use and to maintain sterility of the medical device. For integrated medical devices that combine a dermal tissue penetration member (e.g., a lancet or micro-needle) with a test strip, the associated package should provide for an uncomplicated deployment of the dermal tissue penetration member during use, while also providing for protection of a user from inadvertent contact with the dermal tissue penetration member prior and subsequent to use. Furthermore, the packaging should provide humidity resistance for the test strip during storage.

Single-use (i.e., disposable) integrated medical devices are illustrative of the above requirements in that they require a medical device package that maintains sterility and protects the single-use integrated medical device contained therein from damage prior to use. Such medical device packages should also provide humidity resistance and UV protection for a test strip of such single-use integrated medical devices prior to use. Furthermore, the medical device package should provide for deployment of a dermal tissue penetration member of such a single-use integrated medical device during use, as well as for disabling (i.e., preventing subsequent use) and safely discarding the single-use integrated medical device following use.

Conventional medical device packages do not fulfill all or even most of the requirements described above in a cost effective manner. Still needed in the field, therefore, is a medical device package that provides a sterility barrier and/or for protection of a medical device enclosed therein, while also providing for an uncomplicated deployment of the medical device during use. Furthermore, for integrated medical devices that include a dermal tissue penetration member (e.g., a lancet or micro-needle), a need exists for a medical device package that protects the dermal tissue penetration member from damage, humidity, and/or contamination prior to use, that protects a user from accidental contact therewith and that also disables the medical device following use, thereby preventing its repeated use. In addition, the materials and methods used to manufacture the medical device package should be cost effective.

SUMMARY OF THE INVENTION

Medical device packages according to the present invention provide a sterility barrier and/or protection for a medical device (e.g., an integrated medical device) enclosed therein. Embodiments of medical device packages according to the present invention also provide for an uncomplicated deployment of the medical device during use. Furthermore, with respect to integrated medical devices that include a dermal tissue penetration member (e.g., a lancet or micro-needle), medical device packages according to embodiments of the present invention protect the dermal tissue penetration member from damage, humidity, and/or contamination prior to use, and protect a user from accidental contact therewith. Embodiments of the medical device packages according to the present invention are also adapted to disable the medical device following use, thereby preventing its repeated use. In addition, due to relative simplicity of configuration, medical device packages according to the present invention are cost effective.

A medical device package according to embodiments of the present invention includes a main cap member and a minor cap member. The main cap member has a proximal end, a distal end and a cavity with a cavity opening at the proximal end. The cavity is configured to receive, and to securely and removably retain, a medical device (e.g., an integrated medical device that includes a dermal tissue penetration member and a test strip) at least partially therein. The minor cap member is configured to seal the cavity opening once the medical device has been received in the cavity.

Medical device package kits according to embodiments of the present invention include a main cap member, a minor cap member and a connector. The main cap member has a proximal end, a distal end and a cavity. The cavity has a cavity opening at the proximal end of the main cap member. The cavity is configured to receive, and to securely and removably retain, a medical device at least partially therein. The minor cap member is configured to seal the cavity opening once the medical device has been received in the cavity. The connector is configured to engage the medical device during removal of the medical device from the cavity.

Methods according to the present invention enable the uncomplicated deployment (i.e., extraction) of a medical device from a medical device package. Methods for extracting a medical device from a medical device package according to embodiments of the present invention first include providing a medical device package, with a medical device (e.g., an integrated medical device) therein, and a connector. The provided medical device package includes a main cap member having a cavity and proximal and distal ends, and a minor cap member. The cavity of the main cap member has a cavity opening at the proximal end of the main cap member and is configured to receive, and to securely and removably retain, the medical device at least partially therein. The minor cap member is configured to seal the cavity opening.

The methods also include breaching the minor cap member with the connector such that at least a portion of the connector enters the cavity. Next, the medical device is engaged by the connector and extracted from the medical device package.

Other methods according to the present invention include disabling a medical device that has been extracted from a medical device package by inserting the medical device back into a cavity of the medical device package to a position that results in a disabling of repeated use of the medical device. Such disablement can be obtained by, for example, a wedging of the medical device into a fixed position within the cavity of the medical device package.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings (wherein like numerals represent like elements), of which:

FIGS. 6A and 6B are simplified top and perspective views of an exemplary embodiment of a connector for use with exemplary embodiments of medical device packages according to the present invention;

FIGS. 9A-D are schematic, cross-sectional views depicting various stages of the process of FIG. 8;

FIGS. 14A-D are schematic, cross-sectional views depicting various stages of the process of FIG. 13;

FIGS. 16A and 16B are schematic, top cross-sectional depictions of a stage in the process of FIG. 13;

DETAILED DESCRIPTION OF THE INVENTION

Figure 1:
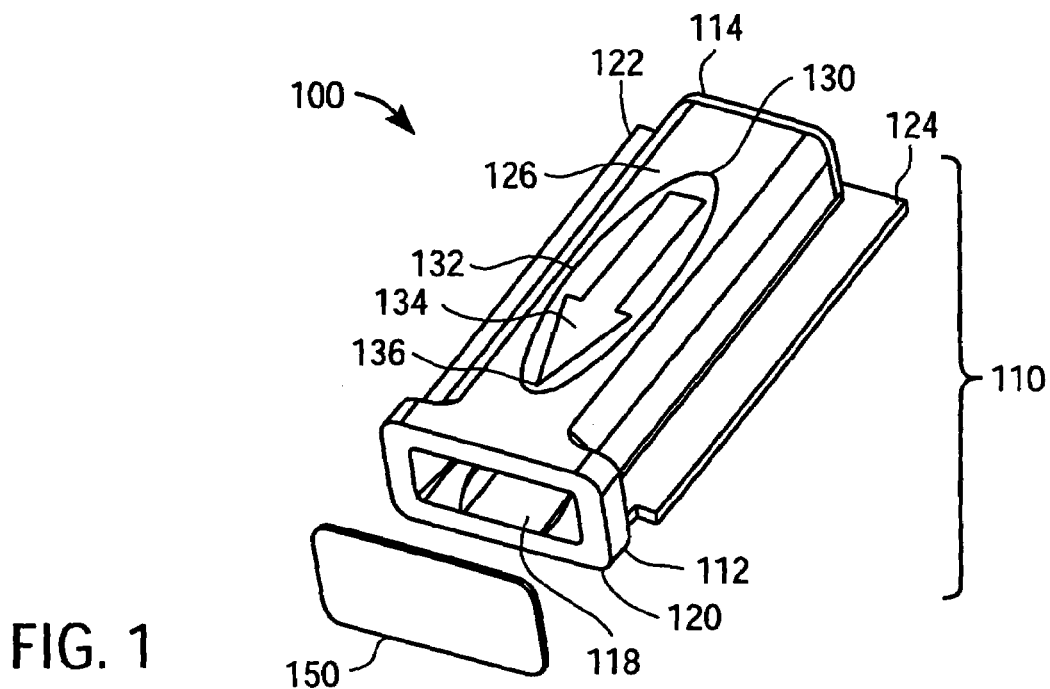
FIG. 1 is a simplified exploded perspective view of a medical device package according to the present invention.

FIGS. 1, 2A-2D, 3A and 3B are various simplified views of a medical device package 100 according to an exemplary embodiment of the present invention. Medical device package 100 includes a main cap member 110 and a minor cap member 150.

Main cap member 110 includes a cavity 116 therein, a proximal end 112 and a distal end 114. Cavity 116 has a cavity opening 118 at the proximal end 112 of the main cap member 110 and is configured to receive, and to securely and removably retain, a medical device (e.g., integrated medical device 300, illustrated in FIGS. 4A and 4B), at least partially therein.

Figure 4A:
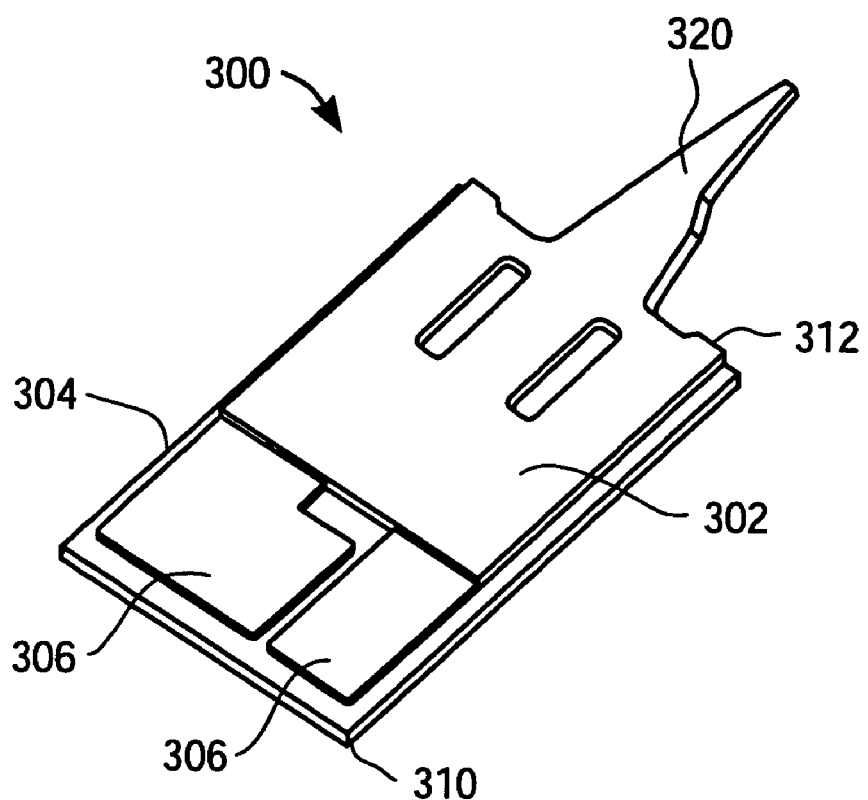
FIGS. 4A and 4B are simplified perspective and side views, respectively of a medical device that can be contained within exemplary embodiments of medical device packages according to the present invention.
Figure 4B:
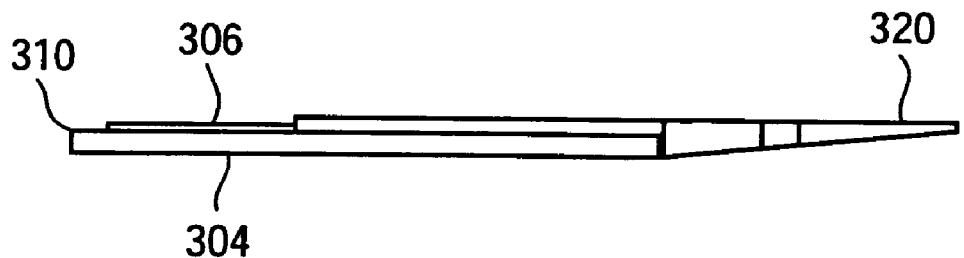
Figure 5A:
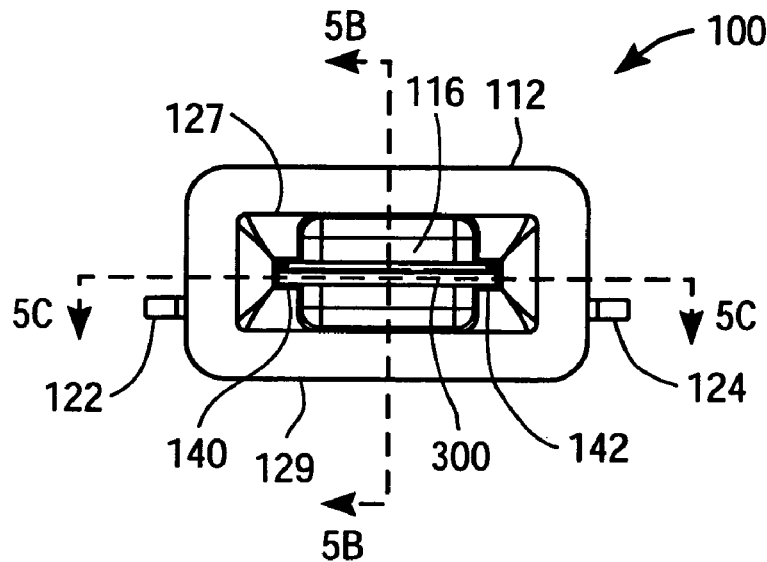
FIG. 5A is a simplified proximal-end view of the main cap member of FIG. 1 containing the medical device of FIGS. 4A and 4B.
Figure 5B:
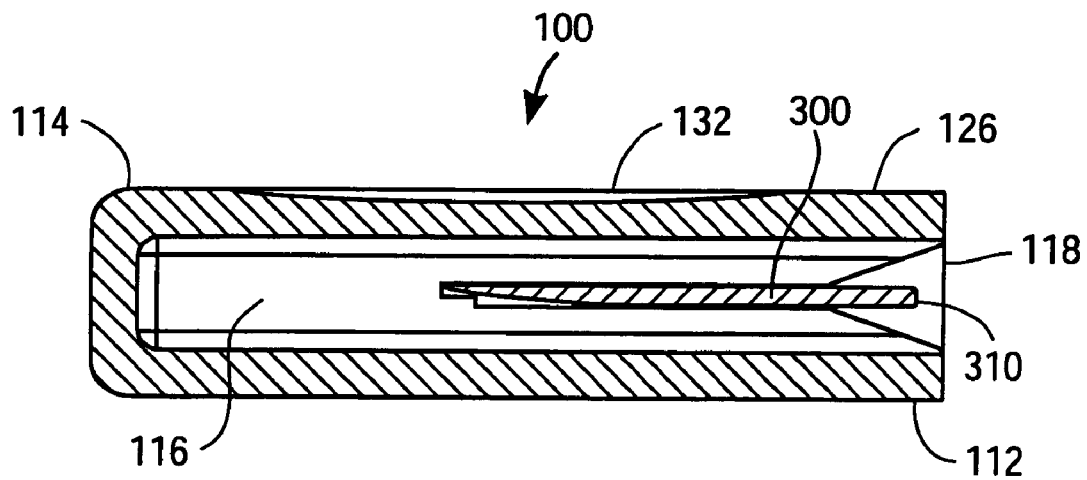
FIG. 5B is a simplified cross-sectional view of the main cap member and medical device of FIG. 5A, representing a view along line 5B-5B of FIG. 5A in the direction of the arrows.
Figure 5C:
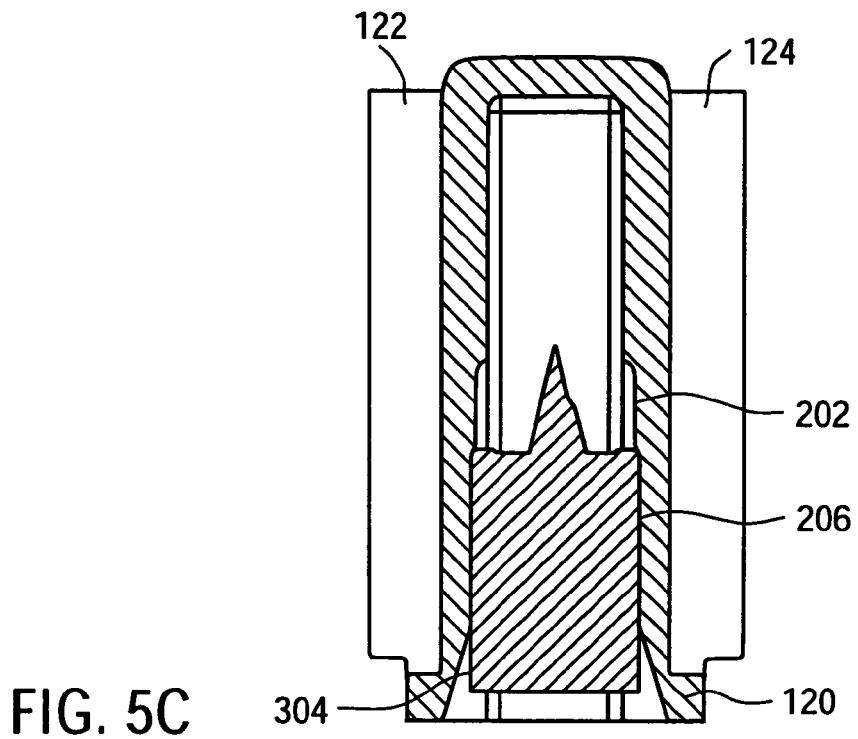
FIG. 5C is a cross-sectional, top view of the main cap member and medical device of FIG. 5A, representing a view along line 5C-5C of FIG. 5A in the direction of the arrows.
Figure 5D:
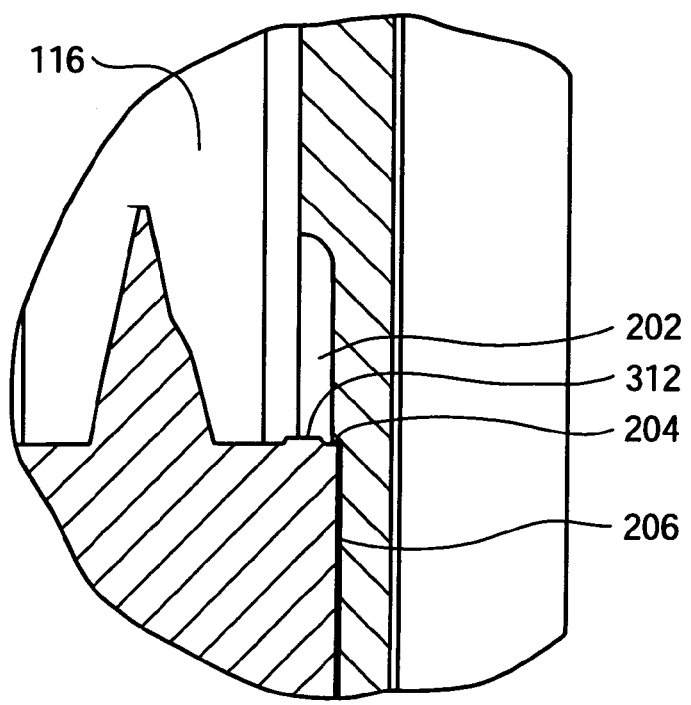
FIG. 5D is an enlargement of a portion of the cross-sectional, top view of the main cap member and medical device of FIG. 5C.

FIGS. 4A and 4B are simplified perspective and side views, respectively, of an exemplary integrated medical device 300 that can be securely and removably contained within medical device package 100. Integrated medical device 300 includes a test strip 304 and a dermal tissue penetration member 302, as illustrated in FIGS. 4A-4B. Test strip 304 has a reaction area (not shown) and electrical contacts 306 that terminate on a distal end 310 of medical device 300. Electrical contacts 306 are made of any suitable conductive material, such as carbon. Dermal tissue penetration member 302 includes a lancet 320 adapted to pierce a user's skin and draw blood into the reaction area of test strip 304. Further descriptions of integrated medical devices that can be contained within embodiments of medical device packages according to the present invention are in International Application No. PCT/GB01/05634 (published as WO 02/49507 on Jun. 27, 2002) and U.S. patent application Ser. No. 10/143,399, both of which are fully incorporated herein by reference. In addition, dermal tissue penetration member 302 can be fabricated, for example, by a progressive die-stamping technique, as disclosed in the aforementioned International Application No. PCT/GB01/05634 (published as WO 02/49507 on Jun. 27, 2002) and U.S. patent application Ser. No. 10/143,399.

Referring again to FIGS. 1, 2A-2D, 3A and 3B, in the embodiment of medical device package 100, cavity opening 118 is bounded by a rim 120 of sufficient surface area to enable minor cap member 150 to be adhered to rim 120 by processes known to those skilled in the art, including, but not limited to, heat sealing processes. In this manner, minor cap member 150 and main cap member 110 of medical device package 100 provide a sterility barrier and humidity protection for a medical device contained therein.

Figure 2A:
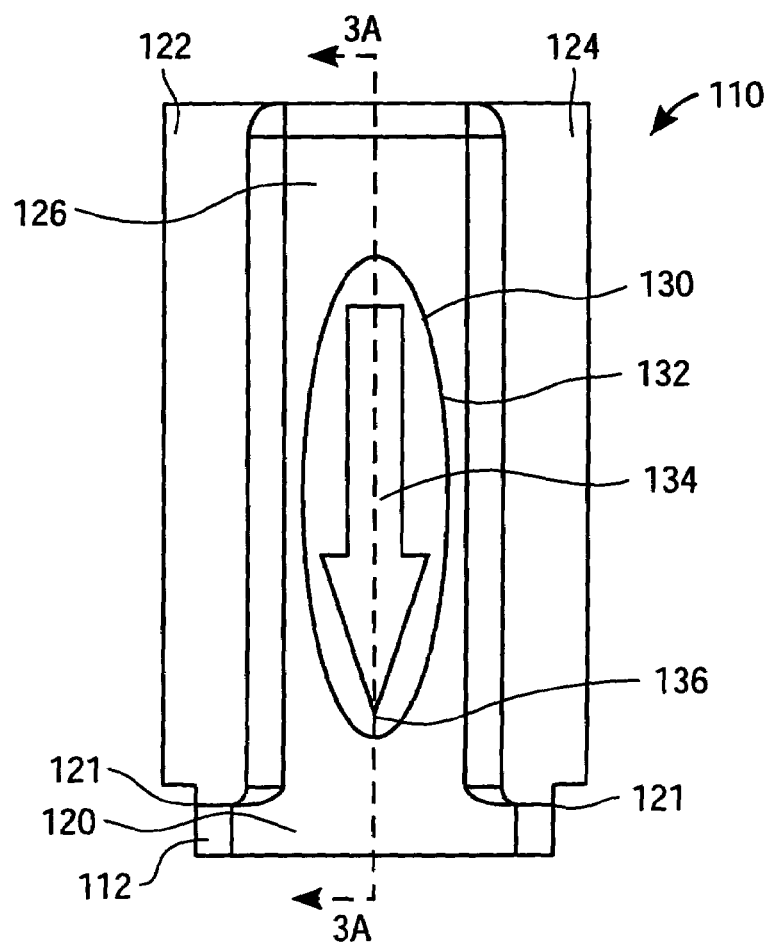
FIGS. 2A-2D are simplified top, side, proximal end and perspective proximal end views of the main cap member of the medical device package of FIG. 1.
Figure 2B:
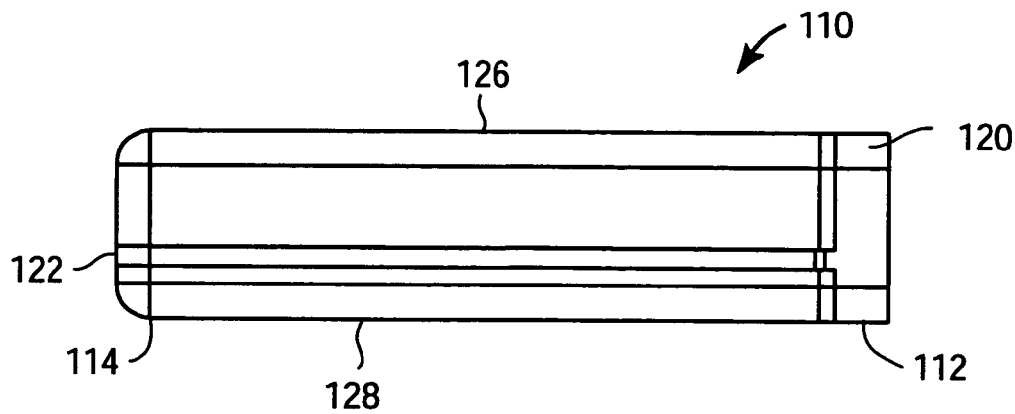

External features of main cap member 110 include a first peripheral edge 122, a second peripheral edge 124, a main cap upper surface 126 and a main cap lower surface 128. As shown in FIG. 2A, first peripheral edge 122 and second peripheral edge 124 are truncated to end at the distal edge 121 of rim 120. If desired, the first and second peripheral edges 122, 124 can be asymmetrically disposed about a longitudinal axis of the main cap member. Such an asymmetric configuration can serve to properly orient the medical device package during its insertion into a receiving slot of associated hardware (for example, an analytical meter receiving slot configured to direct the medical device package to a connector described below with respect to FIGS. 6A-6D).

As shown in FIGS. 1 and 2A, main cap upper surface 126 optionally includes a directional marker 130 that is discontinuous with (e.g., raised above or, alternatively, recessed below) the remainder of main cap upper surface 126. Directional marker 130 may include, but is not limited to, an ellipse 132 and an arrow 134, as depicted in FIGS. 1 and 2A. Directional marker 130 provides a user with both tactile and visual cues for proper orientation of medical device package 100 during use.

Figure 2C:
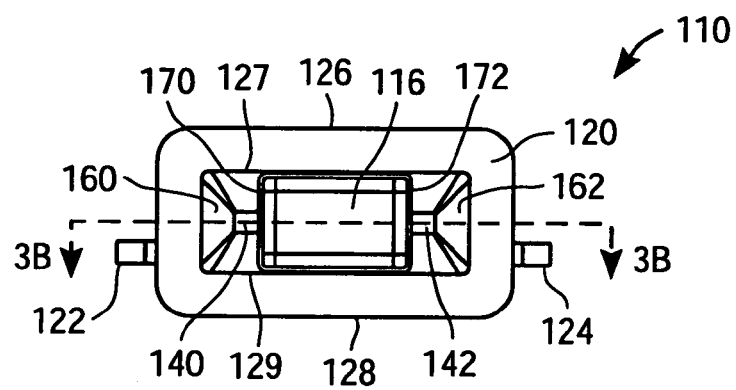
Figure 2D:
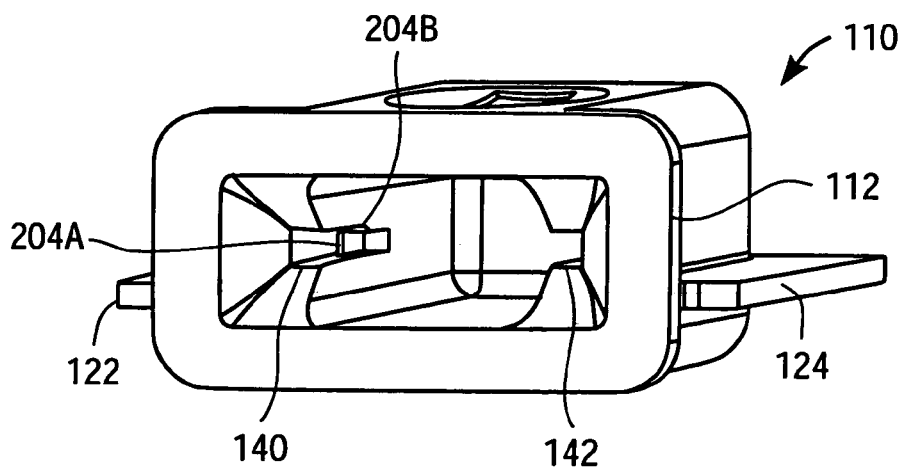
Figure 3A:
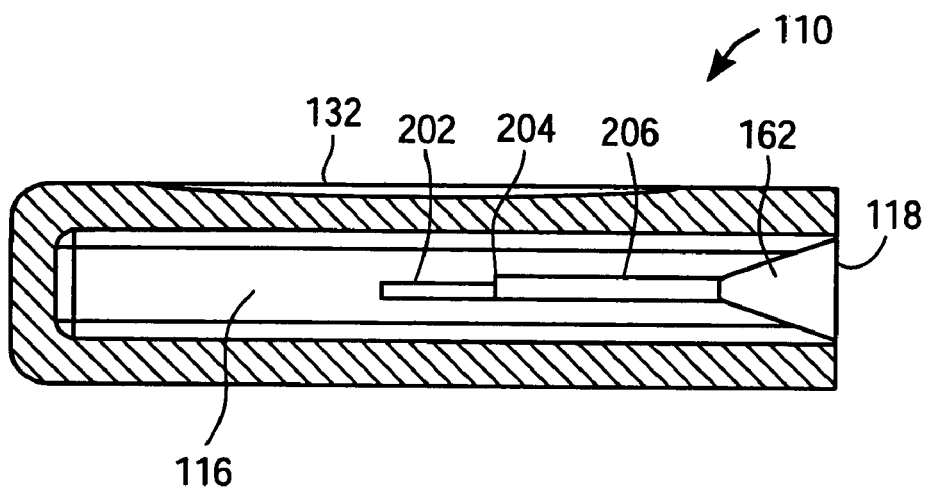
FIG. 3A is a simplified cross-sectional side view of the main cap member of the medical device package of FIGS. 1A through 2D, representing a view along line 3A-3A of FIG. 2A in the direction of the arrows.
Figure 3B:
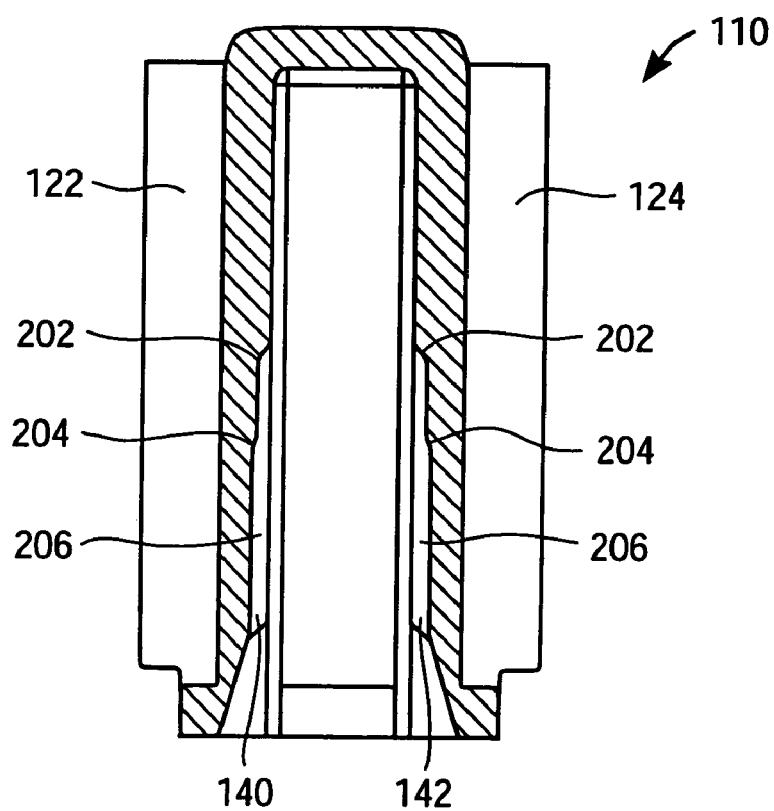
FIG. 3B is a simplified cross-sectional top view of the main cap member of the medical device package of FIGS. 1A through 2D, representing a view along line 3B-3B of FIG. 2C in the direction of the arrows.

Cavity 116 is defined (at least in part) by a first smooth inner surface 127 and a second smooth inner surface 129 and includes first and second lateral channels 140 and 142, respectively, as shown in FIGS. 2C-2D and 3B. In addition, cavity 116 is also defined by first lateral surface 170 located internally to first peripheral edge 122 and a second lateral surface 172 located internally to second peripheral edge 124. In the vicinity of proximal end 112, first lateral surface 170 has a first sloped land 160, and second lateral surface 172 has a second sloped land 162. First sloped land 160 terminates at the beginning of first lateral channel 140, while second sloped land 162 terminates at the beginning of second lateral channel 142. First lateral channel 140 and second lateral channel 142 extend about half way along first and second laterals surfaces 170 and 172, respectively. First and second sloped lands 160, 162 begin at cavity opening 118, and slope inwardly and distally towards distal end 114 of main cap member 110.

First and second lateral channels 140 and 142 begin at the end of first and second sloped lands 160 and 162, respectively, and extend approximately half way into cavity 116. First and second lateral channels 140 and 142 are divided into a post-use portion 202, a transition point 204, and a pre-use portion 206 (see FIGS. 3A and 3B). As is evident from FIG. 3B, first lateral channel 140 is the mirror image of second lateral channel 142. One skilled in the art will recognize from the entirety of the present disclosure that first and second sloped lands 160, 162, first and second lateral channels 140, 142, transition point 204, and pre-use portion 206 are configured to receive, and securely and removably retain, a medical device within cavity 116. In addition, post-use portion 202 is configured to disable a used medical device (as explained in detail below with respect to, for example, FIGS. 16A and 16B).

Main cap member 110 can be formed of any suitable material known to those of skill in the art including, for example, rigid plastic materials such as polystyrene, polycarbonate and polyester. Such rigid plastic materials are impervious to puncturing and to air and/or air-borne bacteria and, therefore, provide a sterility barrier and a puncture-resistant protective barrier. It can be particularly beneficial in terms of humidity protection for main cap member 110 to be formed of a desiccant-loaded high-density polyethylene (e.g., 2AP desiccant-loaded high-density polyethylene, commercially available from Airsec in France).

Minor cap member 150 is configured to seal cavity opening 118 once a medical device has been received in cavity 116. In the embodiment of FIG. 1, minor cap member 150 is a breachable film such as breachable metallic foil. Other suitable materials for minor cap member 150 include paper, polymer and Tyvek. However, as described with respect to other embodiments below, minor cap member 150 can take a variety of forms, all of which are capable of sealing the cavity opening of an associated main cap member once a medical device has been at least partially received within the cavity of the main cap member.

FIG. 2D is a proximal end perspective view of main cap member 110. Transition point 204 includes a vertical shoulder 204A and a horizontal shoulder 204B, as shown in FIG. 2D. Upon insertion of an unused medical device (e.g., integrated medical device 300 of FIGS. 4A and 4B prior to use) into cavity 116 of main cap member 110, vertical shoulder 204A prevents the medical device (not shown) from being inserting past transition point 204 (see FIGS. 2A and 2B). In other words, the unused medical device is inserted only to a first position, which is defined by contact of the unused medical device with transition point 204. However, once a medical device is used, such a used medical device can be inserted back into cavity 116 of main cap member 110 for disablement and disposal purposes. In doing so, the used medical device (e.g., integrated medical device 300 of FIGS. 4A and 4B subsequent to use) is inserted beyond the first position to a second position, wherein the used medical device extends past transition point 204 toward distal end 114 and is irreparably damaged (i.e., disabled) by horizontal shoulder 204B. Such damage prevents a subsequent removal, and thus repeated use, of the once used medical device.

FIGS. 5A-5D are various views of main cap member 100 of FIG. 1 with integrated medical device 300 of FIGS. 4A and 4B inserted therein prior to use of integrated medical device 300 (i.e., integrated medical device 300 is "unused"). In FIGS. 5A-5D, integrated medical device 300 extends between first lateral channel 140 and second lateral channel 142 and lies parallel to first smooth inner surface 127 and second smooth inner surface 129. Unused integrated medical device 300 is securely retained within cavity 116 via a friction fit with first lateral channel 140 and second lateral channel 142. Distal end 310 of integrated medical device 300 remains within proximal end 112 of medical device package 100 and is not in contact with first lateral channel 140 and second lateral channel 142. Furthermore, it should be noted that lancet 320 is within cavity 116 and thus protected from inadvertent damage. Unused integrated medical device 300 is positioned within first and second lateral channels 140 and 142 such that proximal end 312 of integrated medical device 300 touches, but goes no further than, transition point 204, and distal end 310 of integrated medical device 300 remains free from contact with first and second lateral channels 140 and 142 in cavity 116 (see FIGS. 5C and 5D) of main cap member 110.

FIGS. 6A through 6D depict an exemplary embodiment of a connector 500 adapted to extract integrated medical device 300 from medical device package 100. In addition, connector 500 can advantageously be used to mechanically and/or manually manipulate such a medical device once the medical device has been extracted from the medical device package. For example, connector 500 can be used to transfer a medical device from a medical device package to a metering system. As will be appreciated by those skilled in the art, connector 500 may be a component (either a removable component or a permanently integrated component) of a metering system (e.g., an analytical meter configured to determine analyte concentrations in biological fluid samples). Alternatively, connector 500 can be combined with medical device packages to form a kit according to an exemplary embodiment of the present invention.

Connector 500 includes a strip extracting member 502 and a connector body 504. In addition, connector 500 includes a proximal end 510, a distal end 512, an upper surface 514 and a lower surface 516. Connector body 504 includes a connector directional marker 518 on upper surface 514. Connector directional marker 518 (optional) is discontinuous with (e.g., raised above or recessed below) upper surface 514 of connector 500. Connector directional marker 518 may include, but is not limited to, an ellipse 530 and an arrow 532. Connector directional marker 518 provides a user with both tactile and visual cues for proper orientation of connector 500 when inserted into medical device package 100.

Figure 6C:
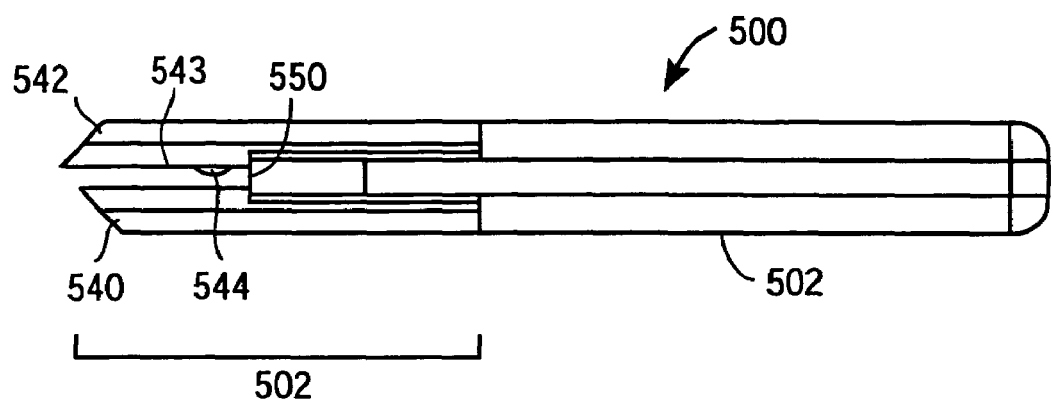
FIG. 6C is a side view of an exemplary embodiment of a connector, representing a view along line 6C-6C in FIG. 6A in the direction of the arrows.
Figure 6D:
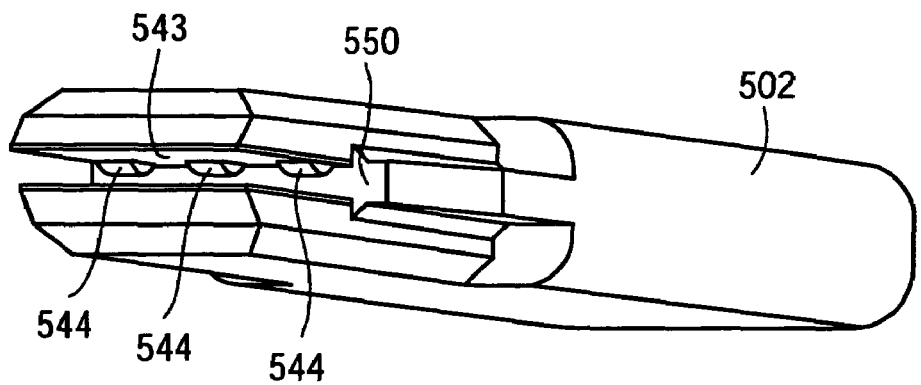
FIG. 6D is a perspective view of the proximal end of an exemplary embodiment of a connector that is used with the preferred embodiment of the medical device package according to the present invention.

Strip extracting member 502 includes a lower strip engaging arm 540, an upper strip engaging arm 542 and a plurality of strip engaging elements 544, as illustrated in FIGS. 6C-6D. Connector 500 also includes electrical leads (not shown) for providing an electrical connection(s) between strip engaging elements 544 and an analytical meter. In addition, strip extracting member 502 includes a vertical barrier 550 that contacts distal end 310 of integrated medical device 300 when integrated medical device 300 is engaged by connector 500. Although three strip engaging elements 544 are depicted in FIG. 6D for the purpose of illustration and explanation, strip extracting member 502 can include any suitable number of strip-engaging elements. Strip engaging elements 544 are located on inner surface 543 of upper strip engaging arm 542. Strip engaging elements 544 are spring-loaded connections formed, for example, by being molded into connector 500 by any suitable process known to those skilled in the art. Strip engaging elements 544 are used to contact test strip 304 of integrated medical device 300 through electrical contacts 306. One skilled in the art will recognize that connector 500 can provide electrical communication between test strip 304 and an analytical meter via strip engaging elements 544 and the connector's electrical leads.

Figure 7:
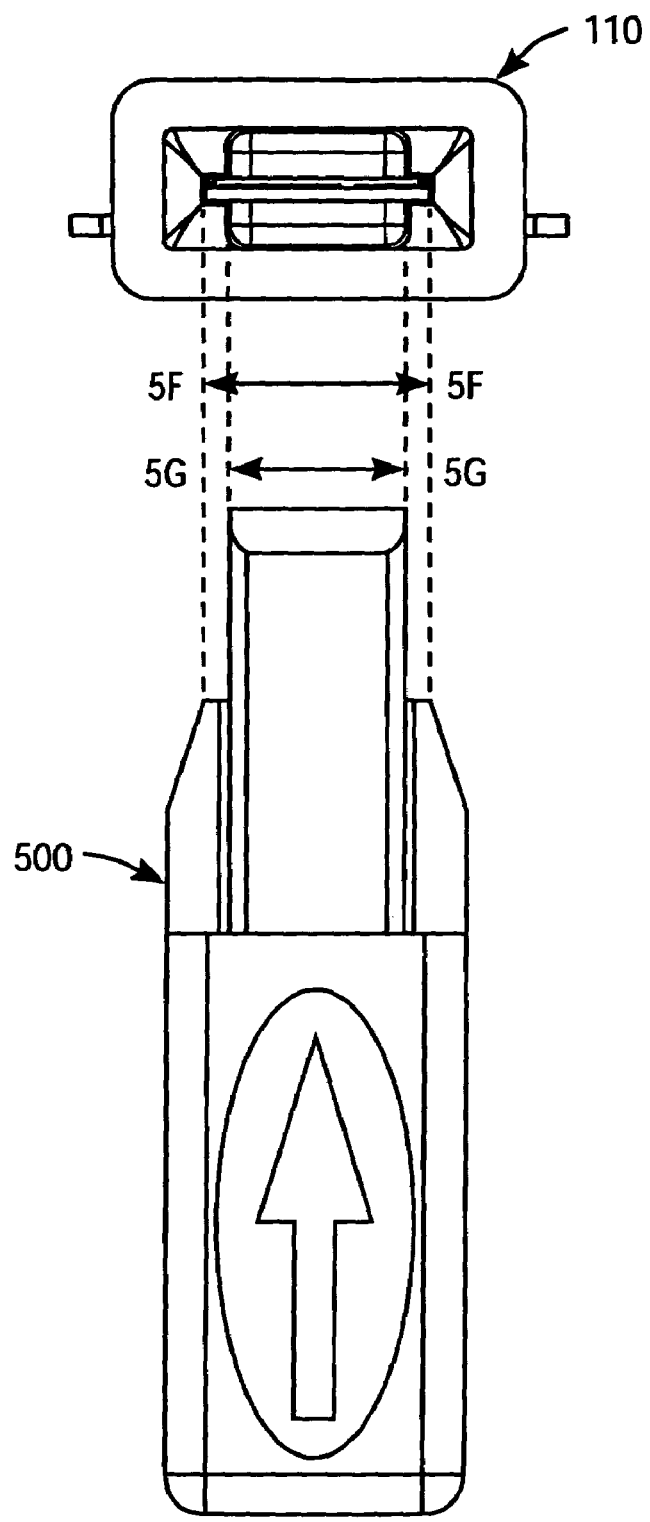
FIG. 7 is a top view of a connector and a proximal end view of an exemplary embodiment of a medical device package according to the present invention.

FIG. 7 is a top view of connector 500 and a proximal end view of main cap member 110, with dashed vertical lines showing proper alignment of connector 500 during extraction of a medical device. Solids horizontal line 5F-5F indicates width of the medical device (for example, approximately 5.5 mm), while solid horizontal line 5G-5G indicates the width of strip extracting element 502 (for example, approximately 4.5 mm).

Figure 8:
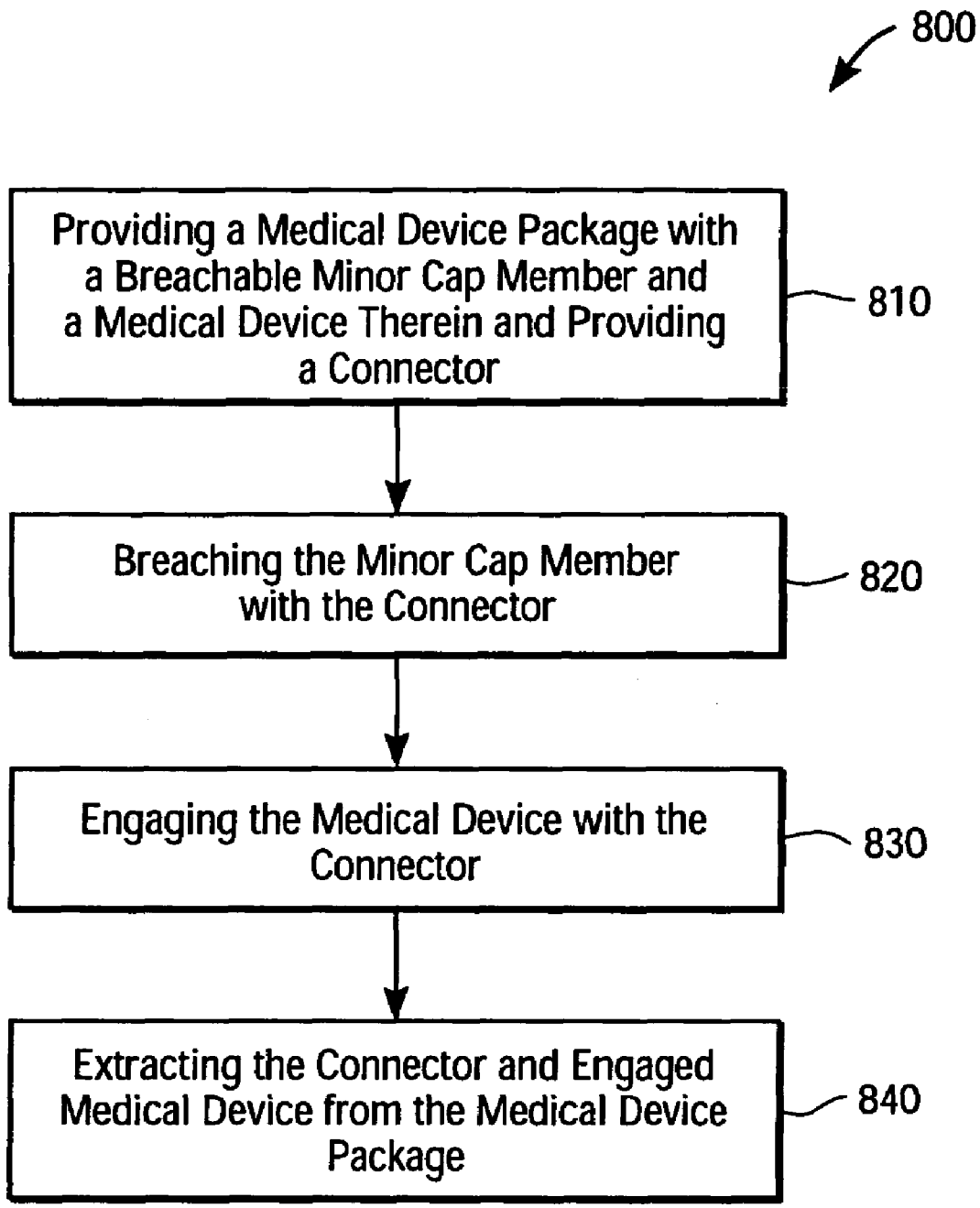
FIG. 8 is a flow chart illustrating a sequence of steps in a process for extracting a medical device from a medical device package according to an exemplary embodiment of the present invention.

FIG. 8 is a flow chart illustrating a sequence of steps in a process 800 for extracting a medical device from a medical device package according to an exemplary embodiment of the present invention. Process 800 is described below utilizing FIGS. 9A-D (schematic, cross-sectional views depicting various stages of process 800), FIGS. 10A-E (schematic, perspective views depicting various stages of process 800), FIGS. 11A-C (schematic, top cross-sectional views of various stages of process 800) and FIGS. 12A-C (schematic enlargements of portions of FIGS. 11A-C, respectively).

Figure 10A:
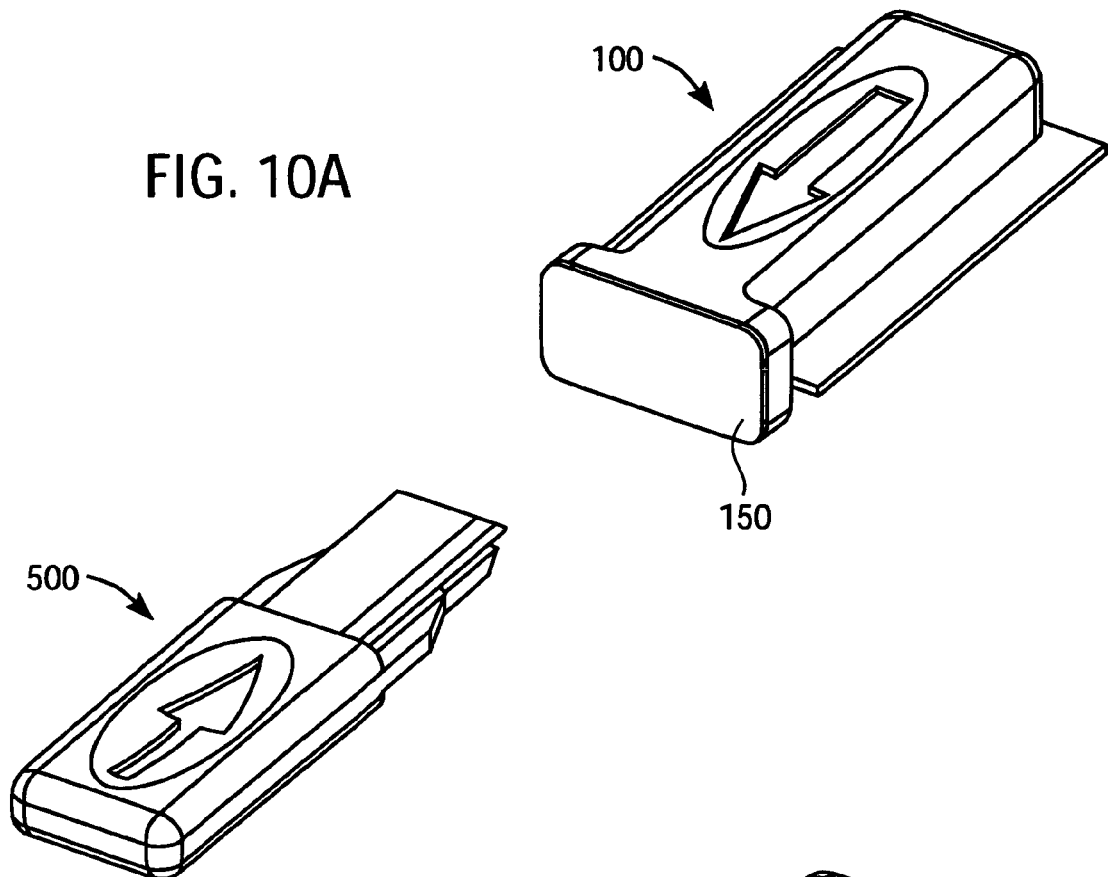
FIGS. 10A-E are schematic, perspective views depicting various stages of the process of FIG. 8.
Figure 10B:
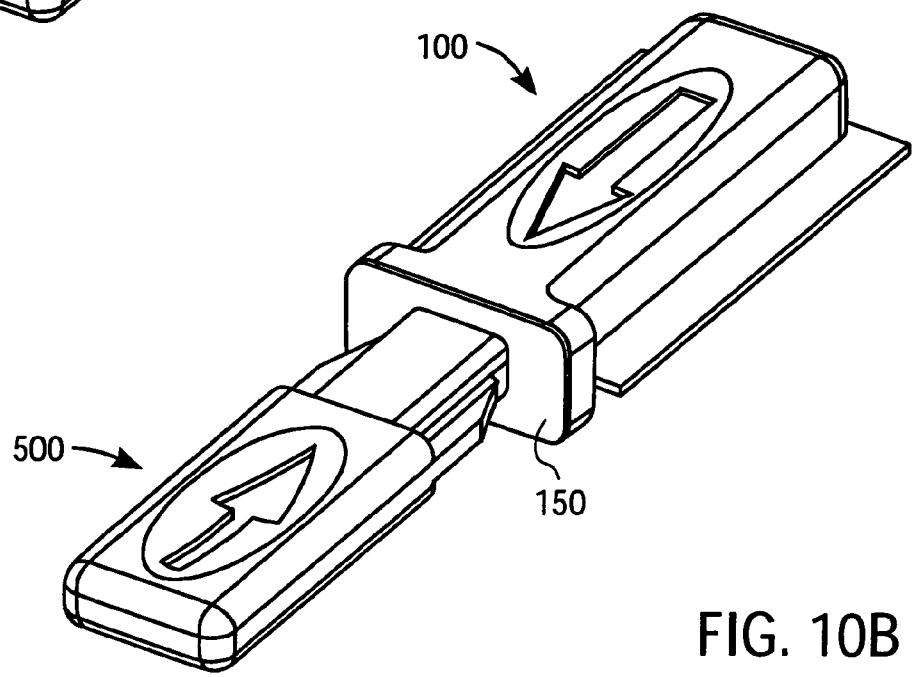
Figure 10C:
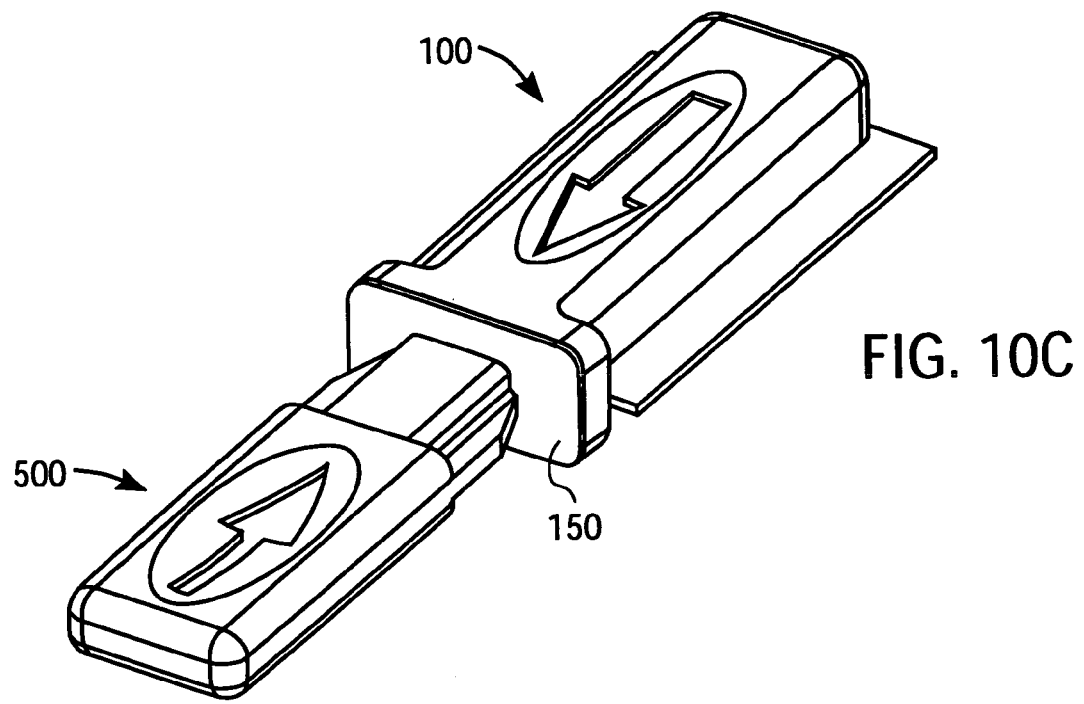
Figure 10D:
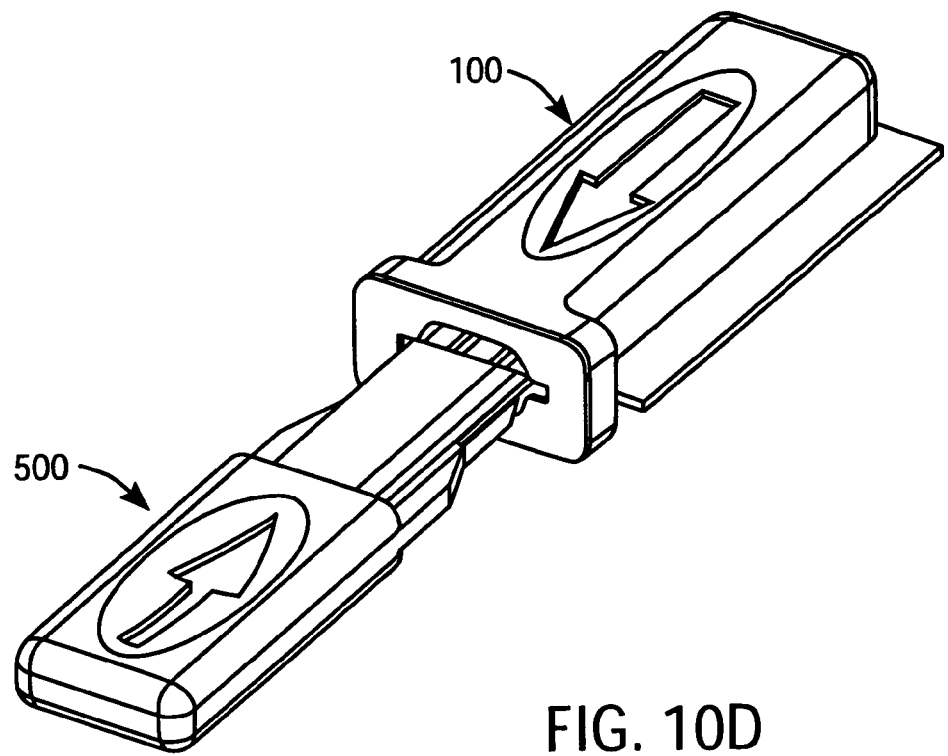
Figure 11A:
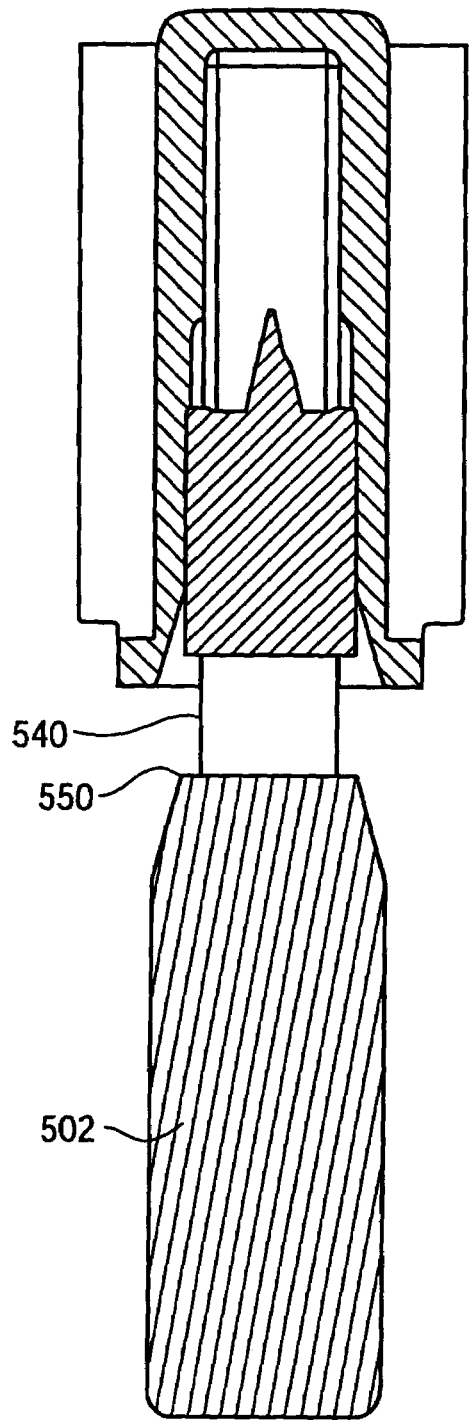
FIGS. 11A-C are schematic, top cross-sectional views depicting various stages of the process of FIG. 8.
Figure 11B:
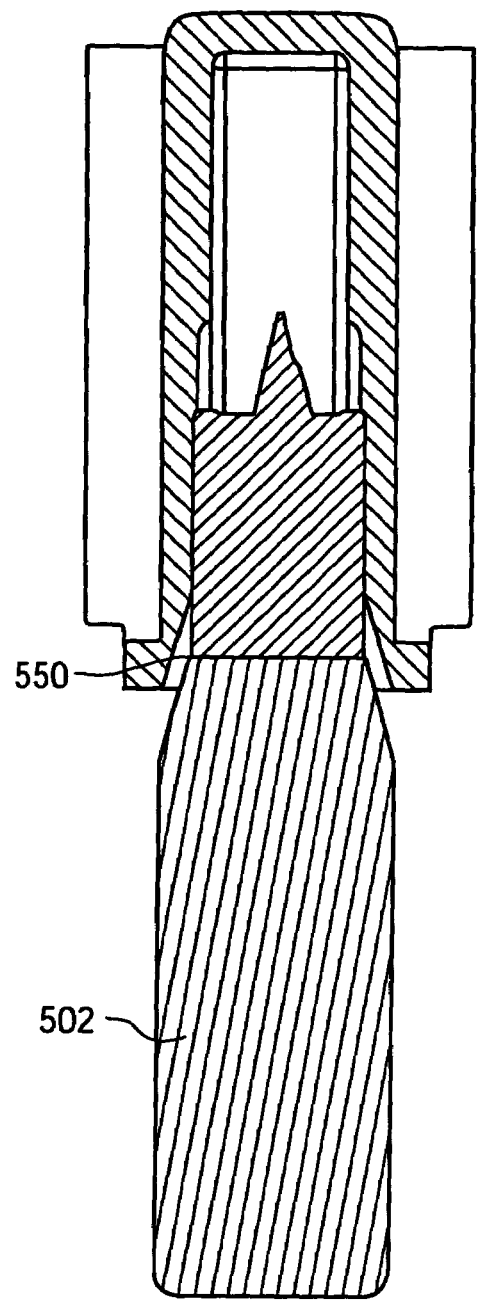
Figure 11C:
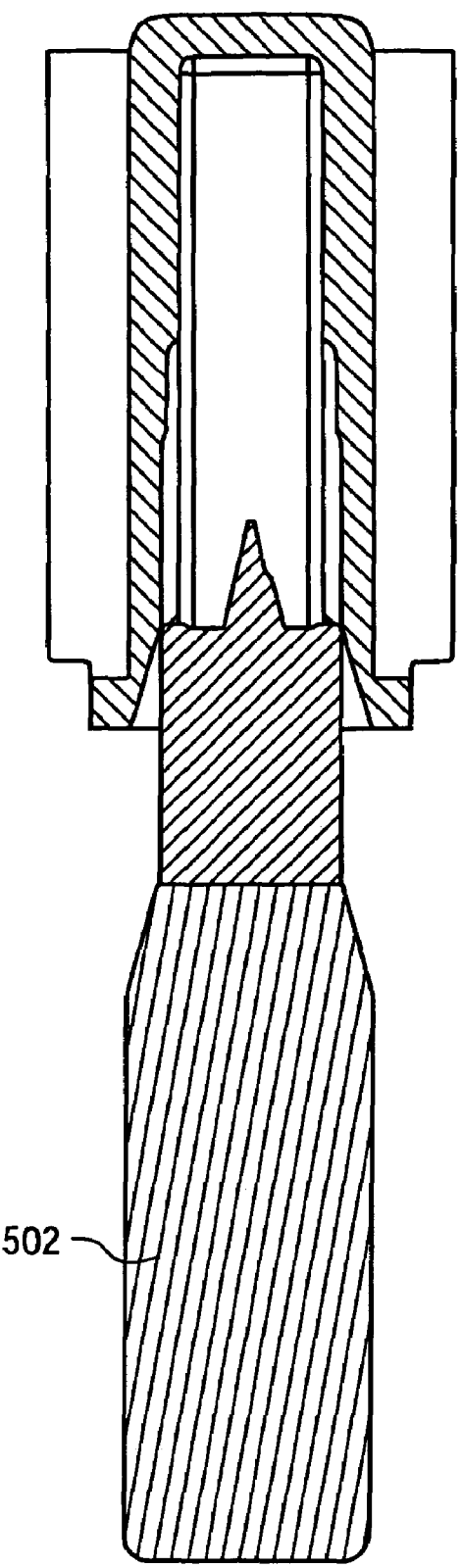

Process 800 includes first providing (i) a medical device package with a minor cap member and a medical device contained therein and (ii) a connector, as set forth in step 810 of FIG. 8. One skilled in the art will recognize that the provided medical device package and connector can be any suitable medical device package according to the present invention that includes a breachable minor cap member (e.g., the medical device package of FIG. 1) and any suitable connector according to the present invention. The provision of an exemplary medical device package and connector are depicted in FIG. 9A and FIG. 10A, wherein like elements of the medical device package and connector of earlier figures are identified with like numerals.

Next, as set forth in step 820, the minor cap member is breached (e.g., ruptured) with the connector such that at least a portion of the connector has entered into the cavity of the main cap member (see FIGS. 9B, 10B, 11A and 12A). Subsequently, the medical device is engaged by the connector (see FIGS. 9C, 10C, 11B and 12B), as set forth in step 830. The force required for the connector to engage with the medical device is, for example, approximately 2N. The connector and engaged medical device are then extracted from the cavity of the medical device package, as set forth in step 840 (see FIGS. 9D, 10D-10E, 11C and 12C). Each of the steps of process 800 can be performed, for example, either manually by a user or with the aid of a mechanical and/or electrical device.

Figure 12A:
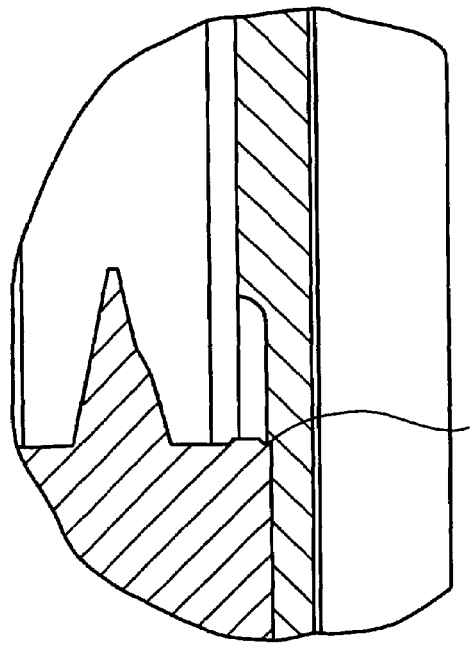
FIGS. 12A-C are schematic enlargements of portions of FIGS. 11A-C, respectively.
Figure 12B:
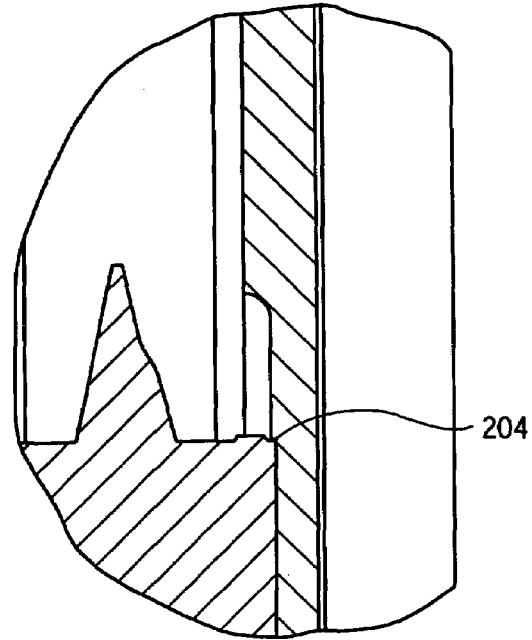
Figure 12C:
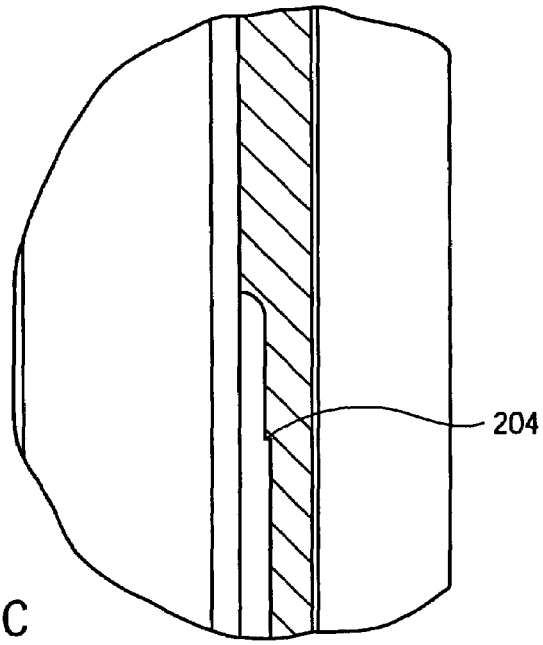

It should be noted, that beaching the minor cap member (such as a breachable film) and engaging the medical device with the connector do not result in the medical device moving past the transition points 204 of the first and second lateral channels 140, 142 (as depicted in FIGS. 12A and 12B, which correspond to the breaching and engaging steps of process 800) since the force required to move the medical device past transition points 204 (e.g., 7N) is significantly greater than the force required to engage the connector with the medical device (e.g., 2N). In the embodiment of FIGS. 9A-9D, 10A-10E, 11A-11C and 12A-12C, during the engaging step, strip engaging elements of the connector engage a test strip 304 of integrated medical device 300 and a vertical barrier of the connector contacts the distal end of the integrated medical device 300. The force required for the breaching the minor cap member and engagement of the medical device can be, for example, in the range of about 1.5 N to 2.5 N.

Figure 10E:
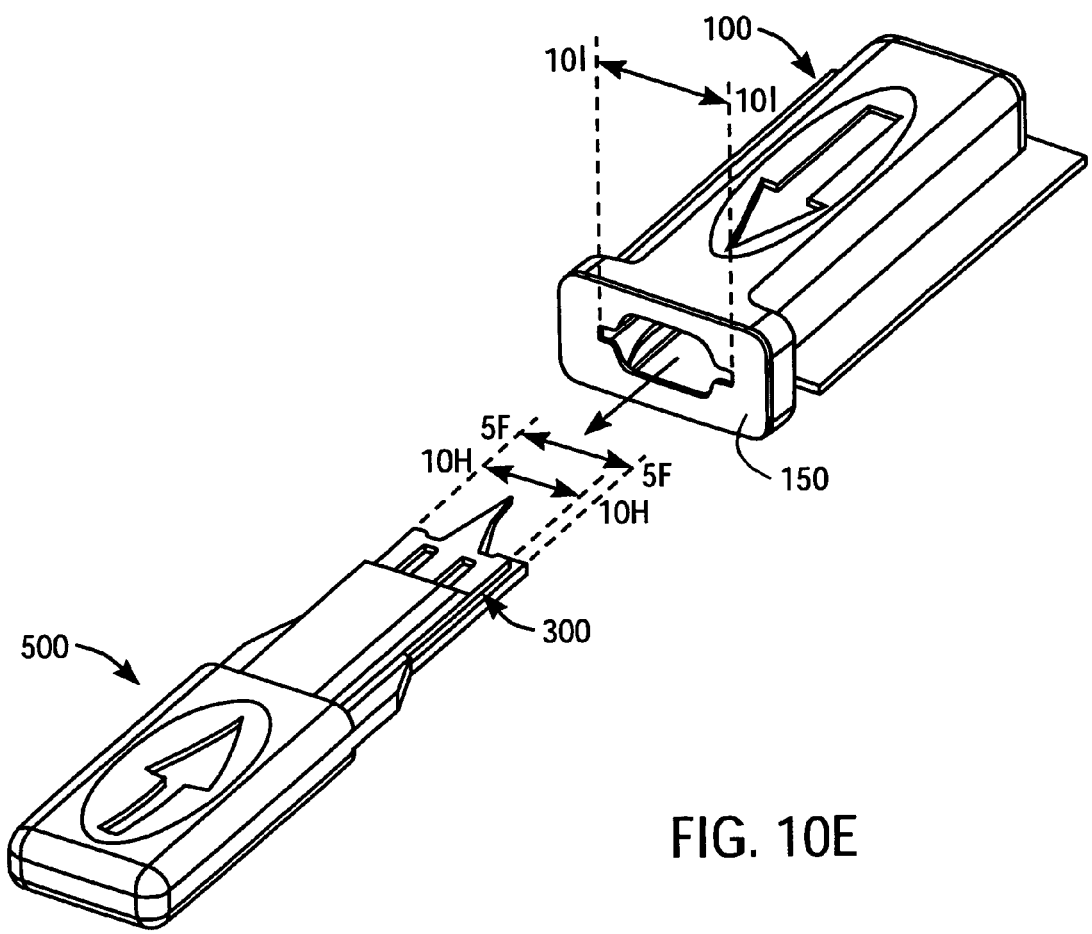

Solid line 5F-5F of FIG. 10E represents a dimension that is identical to the dimension of solid horizontal line 5F-5F of FIG. 7 (i.e., the width of integrated medical device 300). Solid line 10H-10H in FIG. 10E represents the width of the medical device's lancet. Solid line 101-101 of FIG. 10E represents the width of cavity opening of medical device package, which is larger than the dimension represented by solid line 5F-5F to assure a medical device's smooth insertion into, and removal from the cavity.

Process 800 can be performed manually or automatically. Furthermore, process 800 can be, for example, performed by an integrated device that combines an analytical meter and a connector in a configuration that provides for (i) a medical device to be extracted from a medical device package; (ii) a sample (e.g., a whole blood sample) to be obtained from a user and (iii) an analytical result (e.g., blood glucose concentration of the whole blood sample) to determined, all by a single operation of the integrated device. Mechanical motions may be incorporated into a lancet cocking action, new test strip deployment and/or ejection.

Figure 13:
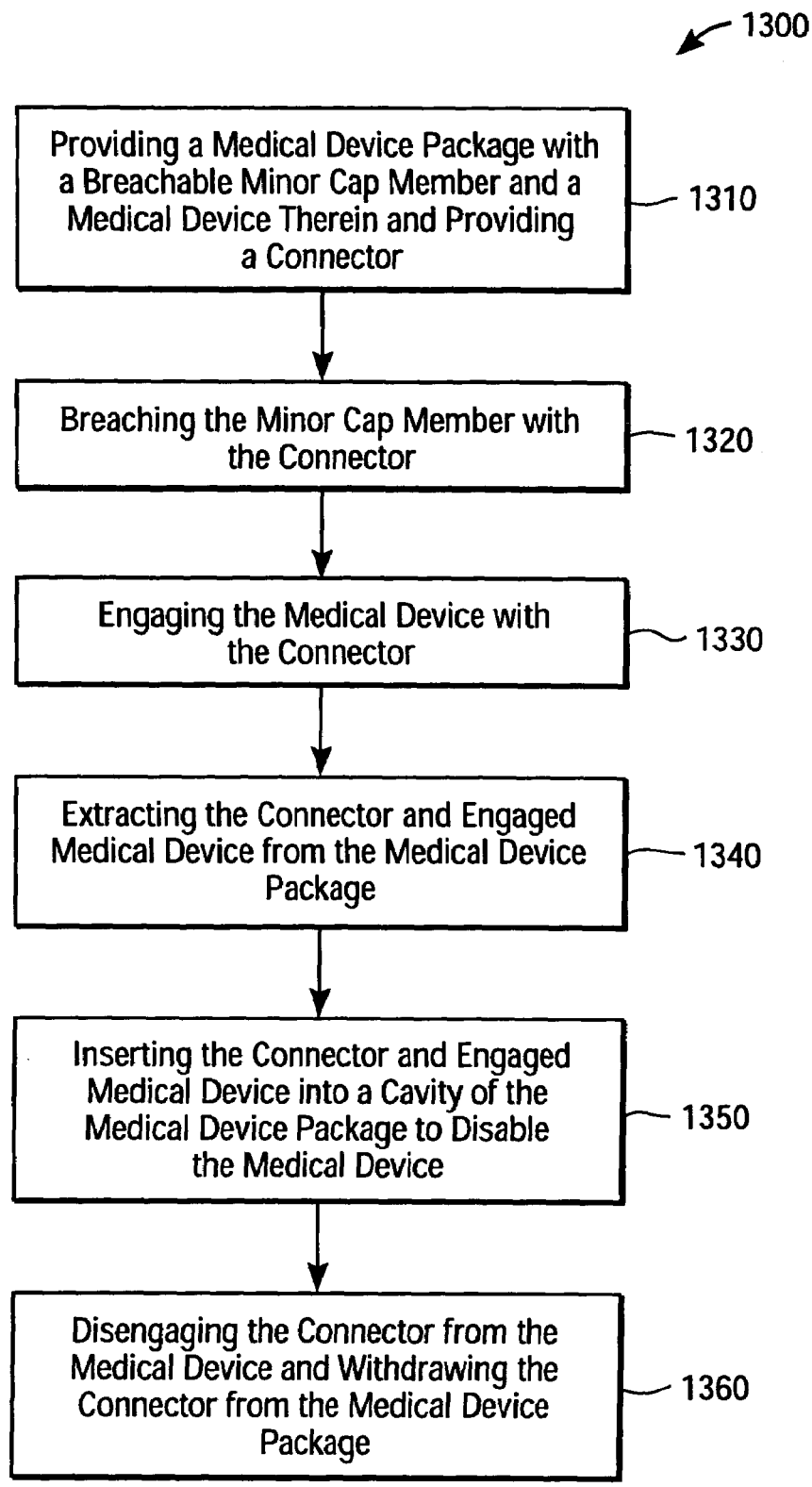
FIG. 13 is a flow chart illustrating a sequence of steps in a process for extracting a medical device from a medical device package and subsequently disabling the medical device according to an exemplary embodiment of the present invention.
Figure 14C:
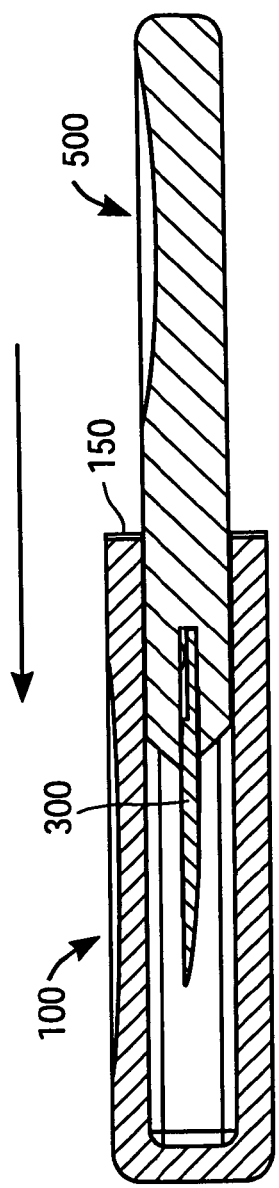
Figure 14D:
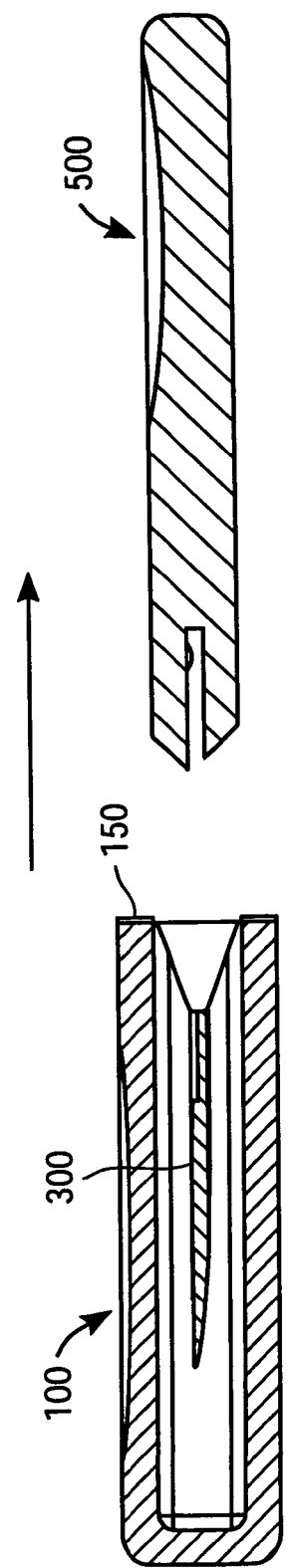
Figures 15A, 15B:
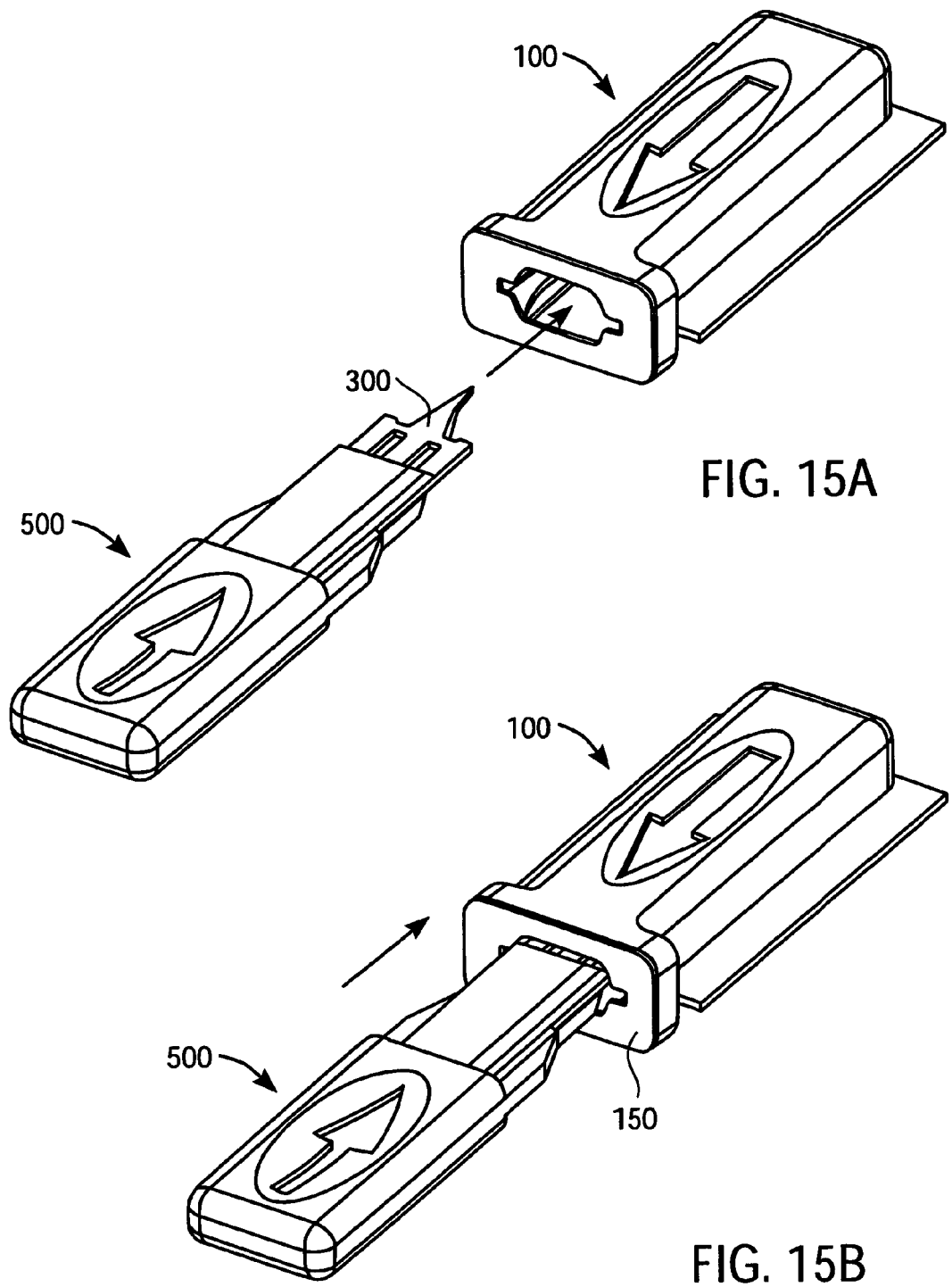
FIGS. 15A-D are schematic, perspective views depicting various stages of the process of FIG. 13.
Figure 15C:
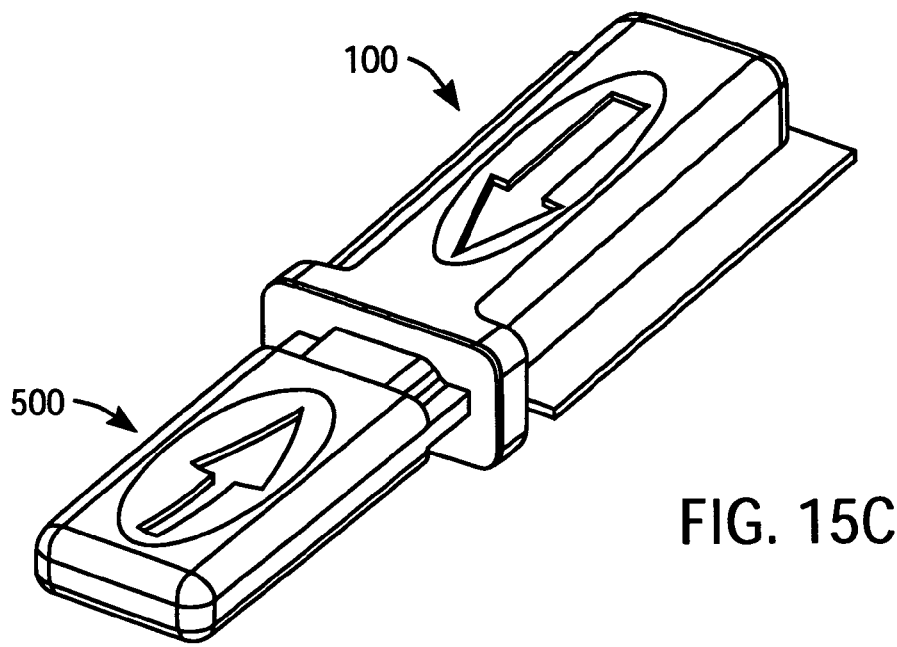
Figure 15D:
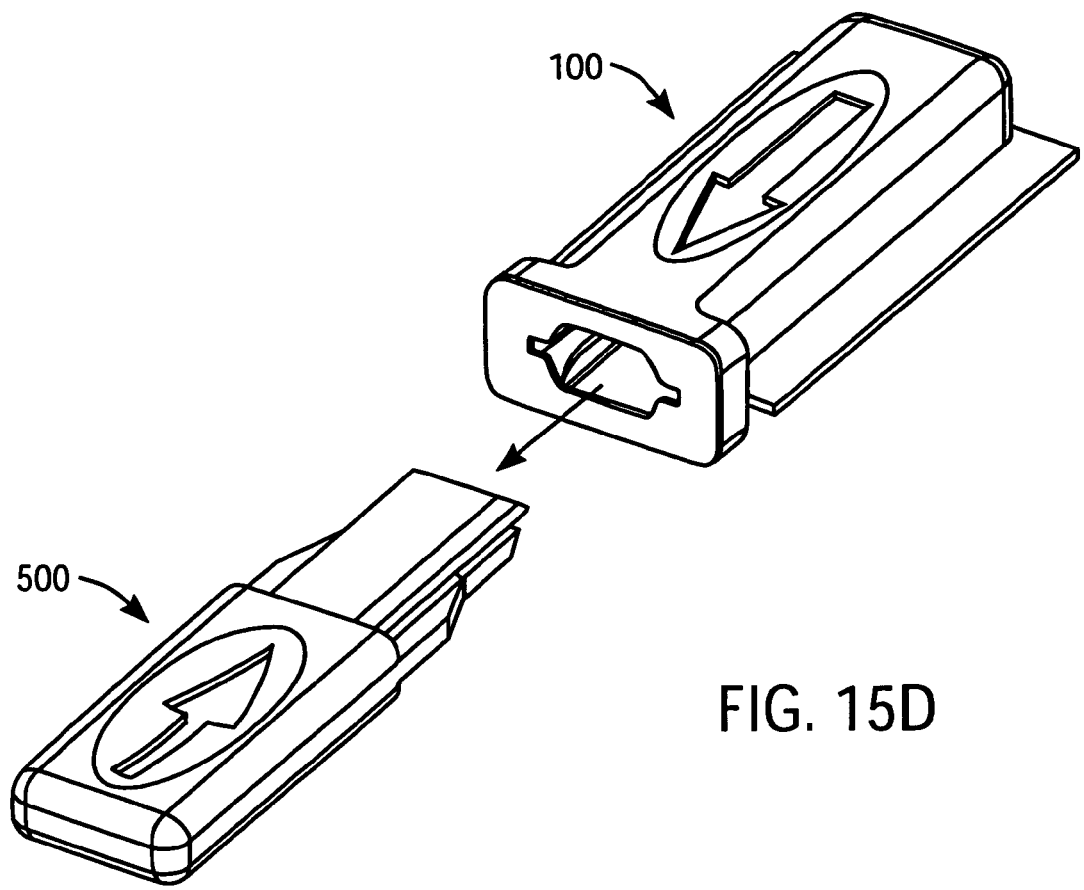

FIG. 13 is a flow chart illustrating a sequence of steps in a process 1300 for extracting a medical device from a medical device package for use and subsequently disabling the medical device after use according to an exemplary embodiment of the present invention. Process 1300 is described below utilizing FIGS. 14A-14D (schematic, cross-sectional views depicting various stages of process 1300), FIGS. 15A-15D (schematic, perspective views depicting various stages of process 1300) and FIGS. 16A-16B (schematic, top cross-sectional views of a stage of process 1300).

Process 1300 includes first providing (i) a medical device package with a minor cap member and a medical device contained therein at a first position and (ii) a connector, as set forth in step 1310 of FIG. 13. One skilled in the art will recognize that the provided medical device package and connector can be any medical device package according to the present invention that includes a breachable minor cap member (e.g., the medical device package of FIG. 1).

Next, at step 1320, the minor cap member is breached (e.g., ruptured) with the connector such that at least a portion of the connector has entered the cavity of the main cap member. The medical device is then engaged by the connector, as set forth in step 1330. The connector and engaged medical device are then extracted from the cavity of the medical device package for use, as set forth in step 1340.

Subsequently, at step 1350, the connector and engaged medical device are inserted back into a cavity of the medical device package to a second position, whereby the medical device is disabled from reuse (see FIGS. 14A-14C, 15A-15C and 16A-16B). The connector is then disengaged from the medical device and withdrawn from the medical device package, as set forth in step 1360. It is envisioned that during step 1350, the medical device is disabled by virtue of the medical device being wedged into the cavity such that the force required to remove the medical device from the cavity is greater than the force required to disengage the connector from the medical device. Therefore, an attempt to re-extract the medical device with the connector would be unsuccessful since the connector would become disengaged from the medical device before sufficient force could be applied to extract the wedged medical device.

It should be noted that during insertion of the connector and engaged medical device into the cavity at step 1350, the medical device is inserted to a second position within post-use portion 202 that is beyond transition points 204 of the first and second lateral channels (see, in particular, FIG. 16B), i.e., beyond the first position. The force required to insert the medical device into the medical device package and disable the medical device is, for example, approximately 7N. As noted above, disablement of the medical device is a result of the medical device being wedged into the cavity such that it cannot be re-extracted using the connector.

Figure 17:
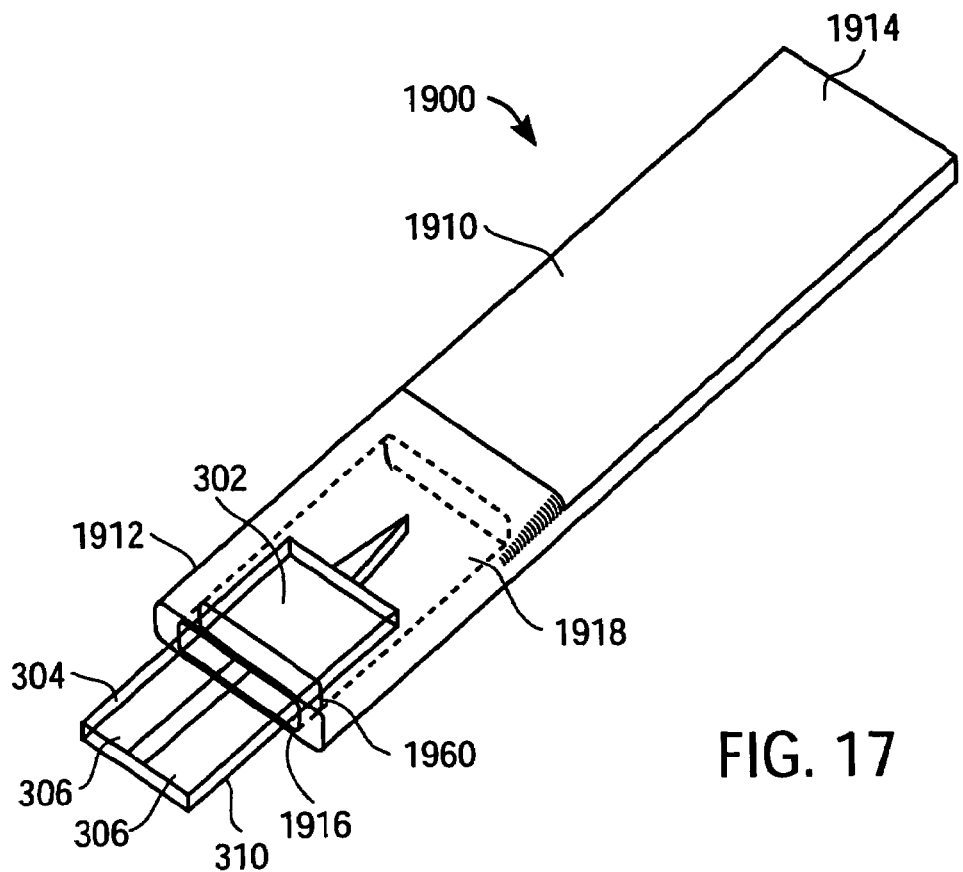
FIG. 17 is a simplified perspective view of a medical device package according to another exemplary embodiment of the present invention containing a medical device.

FIG. 17 depicts a medical device package 1900 according to another exemplary embodiment of the present invention. In FIG. 17, dashed lines indicate certain features that are hidden due to the perspective nature of FIG. 17. In addition, FIG. 17 depicts the circumstance where a medical device (i.e., integrated medical device 300 of FIGS. 4A and 4B) is retained partially within medical device package 1900. In the embodiment of FIG. 17, electrical contacts 306 project from the cavity opening and minor cap member. Since electrical contacts 306 project from both the cavity opening and the minor cap member, engagement of the electrical contacts with a connector can be simplified. For example, there is no need to breach or otherwise remove any component of the medical device package to obtain access to the electrical contacts and the electrical contacts are free to deflect upon engagement with a connector.

Medical device package 1900 includes a main cap member 1910 with a proximal end 1912, a distal end 1914, a cavity 1918 and a cavity opening 1916. Distal end 1914 is configured to function as a handle during manually removal of medical device package 1900 from secondary packaging (not illustrated).

Medical device package 1900 can be constructed, for example, of molded plastic or other material that is impervious to air and/or air-borne bacteria, to provide a sterile-protective and puncture-resistant barrier. Suitable materials include, but are not limited to, polystyrene, polyethylene, polycarbonate and polyester.

Cavity 1918 of medical device package 1900 is defined by surfaces depicted with dashed lines in FIG. 17. Cavity opening 1916 is configured to provide for the placement of dermal tissue penetration member 302 of medical device 300 wholly within cavity 1918, as shown in FIG. 17. Medical device package 1900 includes internally disposed ribs 1960, located distally to cavity opening 1916. Ribs 1960 serve to seal cavity 1918 once a medical device has been inserted partially therein, and provide a sterile and protective barrier for dermal tissue penetration member 302 by creating a tortuous path between the external environment and the cavity of the medical device package. Ribs 1960, together with an at least partially inserted medical device, serve as a minor cap member for medical device package 1900. As an alternative to ribs 1960, elastomeric o-rings could be employed to seal cavity 1918 once a medical device has been inserted partially therein, and to provide a sterile and protective barrier for dermal tissue penetration member 302.

Figure 18:
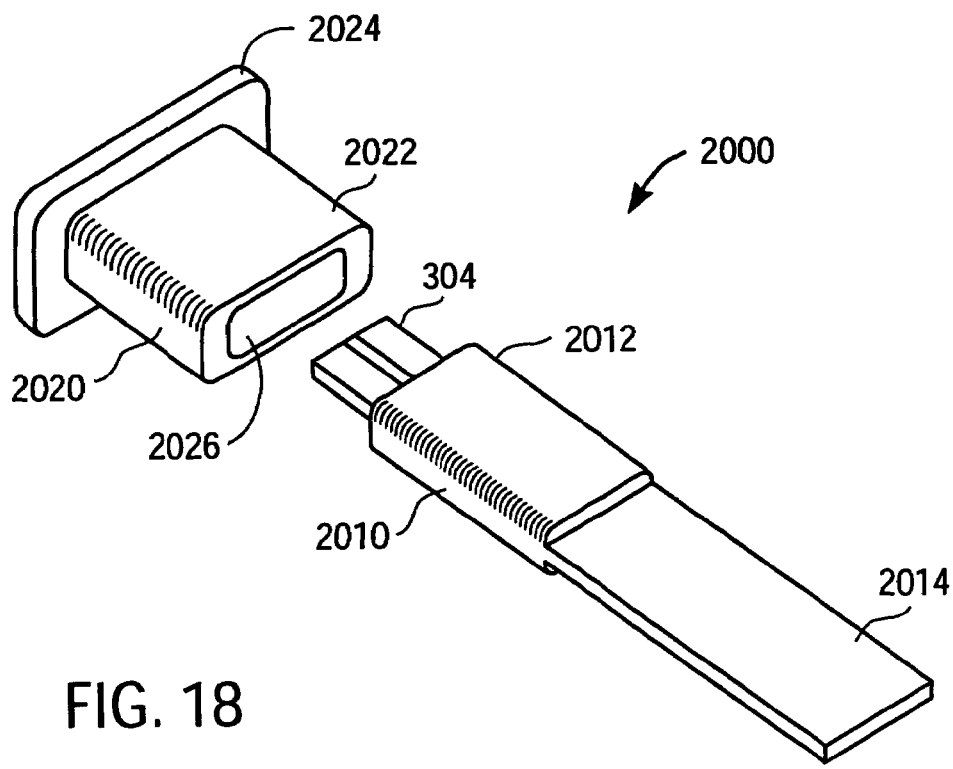
FIG. 18 is an exploded perspective view of yet another exemplary embodiment of a medical device package containing an integrated medical device according to the present invention.

FIG. 18 is an exploded perspective view of a medical device package 2000 according to yet another exemplary embodiment of the present invention containing a medical device 300 (as depicted in FIGS. 4A and 4B). Medical device package 2000 includes a main cap member 2010 and a minor cap member 2020. Main cap member 2010 has a proximal end 2012, a distal end 2014, a cavity opening (not shown), and a cavity (also not shown). The cavity and cavity opening of main cap member 2010 are configured for placement of a dermal tissue penetration member of an integrated medical device wholly therein, thus providing a protective barrier for such a dermal tissue penetration member.

Minor cap member 2020 has a proximal end 2022, a distal end 2024, a minor cap opening 2026, and a minor cap cavity (not shown in FIG. 18). Minor cap opening 2026 and the minor cap cavity are configured for the placement of a test strip 304 of an integrated medical device wholly or partially therein. Furthermore, proximal end 2012 of main cap member 2010 is adapted to fit wholly within minor cap opening 2026 and the minor cap cavity. Once main cap member 2010 is fit within minor cap opening 2026 and the minor cap cavity, integrated medical device 300 is completely enclosed and provided with a sterile-protective and moisture-free barrier.

Both main cap member 2010 and minor cap member 2020 are beneficially constructed of molded plastic or other rigid material that is impervious to air and/or air-borne bacteria, to provide a sterile-protective and puncture-resistant barrier. Suitable materials for main cap member 2010 and minor cap member 2020 include, but are not limited to, polystyrene, polyethylene, polycarbonate and polyester.

Figure 19:
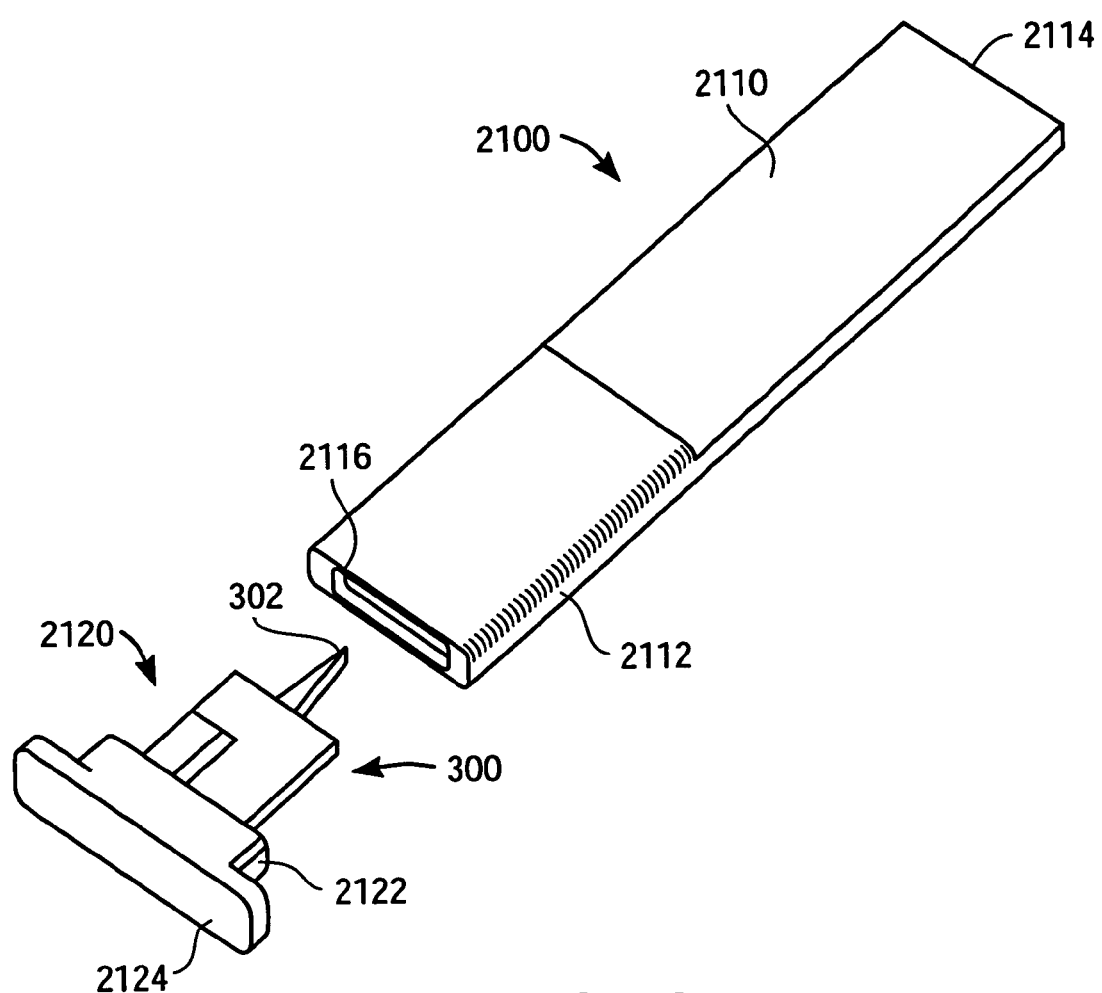
FIG. 19 is an exploded perspective view of yet another exemplary embodiment of a medical device package containing an integrated medical device according to the present invention.

FIG. 19 is an exploded perspective view of a medical device package 2100 according to yet another exemplary embodiment of the present invention. Medical device package 2100 includes a main cap member 2110 and a minor cap member 2120. Main cap member 2110 has a proximal end 2112, a distal end 2114, a cavity opening 2116 and a cavity (not shown). Cavity opening 2116 and the cavity of medical device package 2100 are configured for placement of a dermal tissue penetration member 302 of an integrated medical device and a minor cap member proximal end 2122 (described below) wholly therein, thus providing a protective barrier for dermal tissue penetration member 302.

Minor cap member 2120 of medical device package 2100 has a proximal end 2122 and a distal end 2124. Moreover, integrated medical device 300 is permanently attached to minor cap member 2120 at proximal end 2122. The permanent attachment of such an integrated medical device to minor cap member 2120 is envisioned to provide handling benefits during use of the integrated medical device. For example, minor cap member 2120 could be gripped by a meter, with the main cap member then being easily removed by a user (e.g., by pulling, twisting or snapping) to deploy the integrated medical device.

Figure 20:
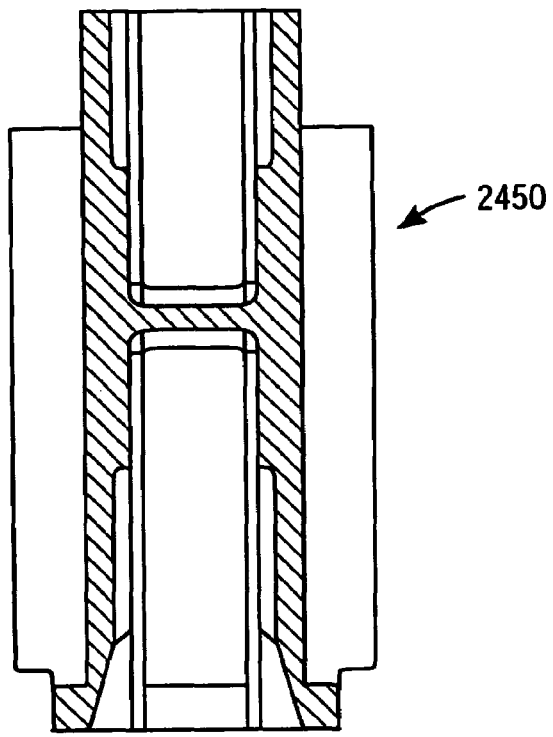
FIG. 20 is a simplified cross-sectional top view of an additional exemplary embodiment of a medical device package according to the present invention.
Figure 21:
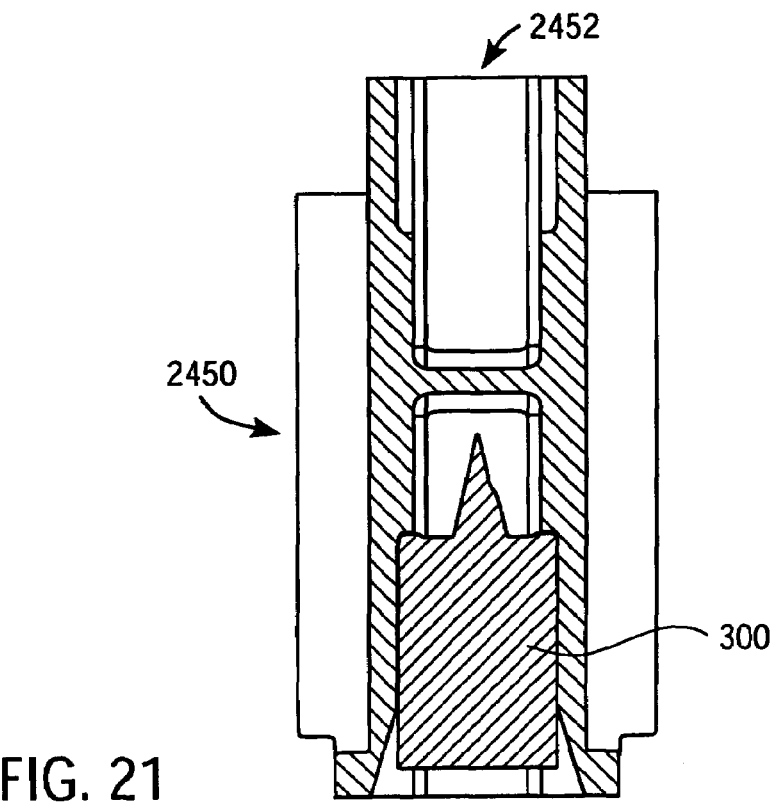
FIG. 21 is a simplified cross-sectional top view of the medical device package of FIG. 20 with a medical device retained therein.
Figure 22:
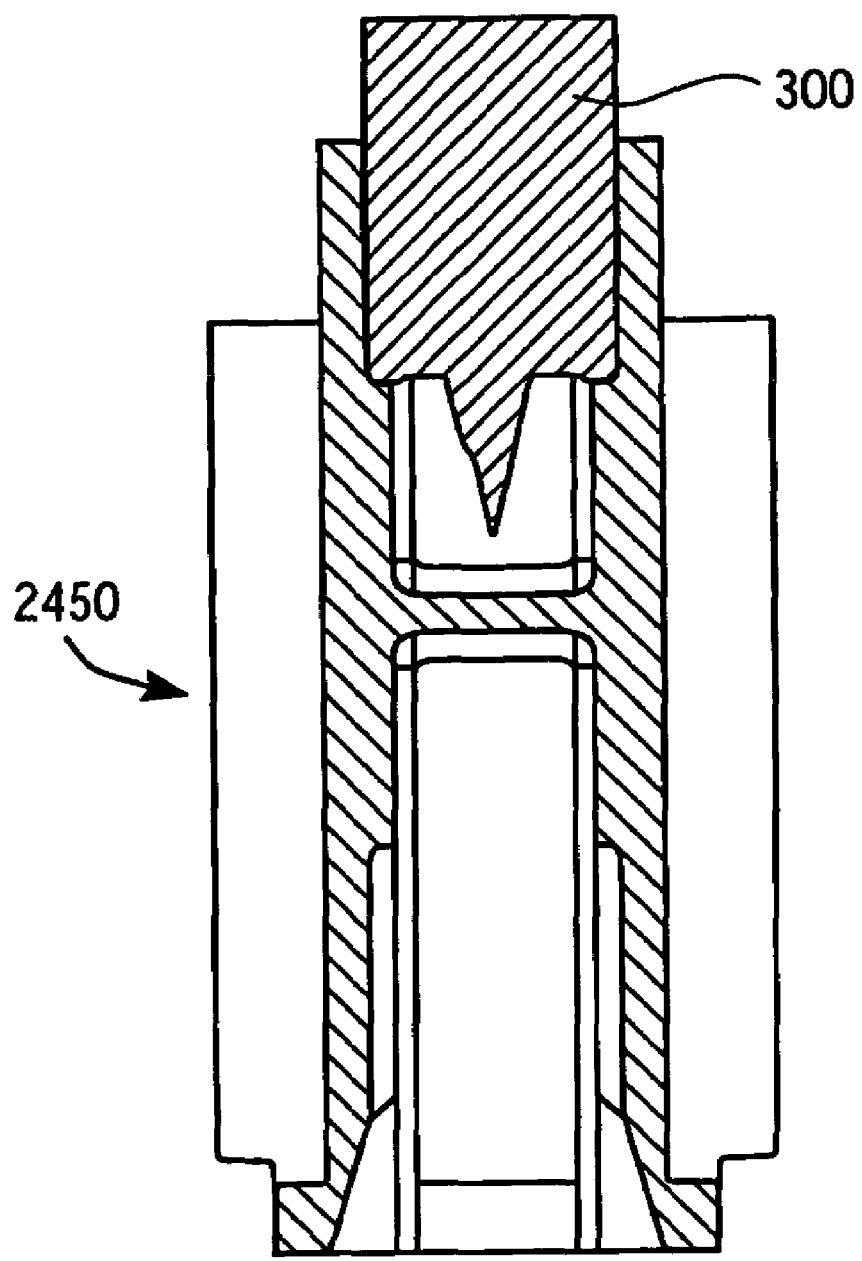
FIG. 22 is a simplified cross-sectional top view of the medical device package of FIG. 21 with a medical device disabled therein.

FIGS. 20, 21 and 22 depict the main cap member 2450 of a medical package device according to yet another exemplary embodiment of the present invention (for purposes of clarity, the minor cap member of this medical device package is not illustrated). FIG. 21 depicts an integrated medical device 300 retained within main cap member 2450 and FIG. 22 depicts an integrated medical device 300 disabled within main cap member 2450. Main cap member 2450 is identical to main cap member 110 of FIG. 3B, with the exception that main cap member 2450 has a distal end cavity 2452 configured for disablement and disposal of an integrated medical device.

Those skilled in the art will recognize that embodiments of medical device packages according to the present invention can be secondarily packaged for single use in, for example, a vial or cartridge configured for dispensing the medical device packages. The secondary package may be constructed of material containing desiccant or may contain separately packaged desiccant for maintaining contents moisture free.

Once apprised of the present disclosure, one skilled in the art will also recognize that a variety of medical devices can be beneficially employed with embodiments of medical device packages according to the present invention. Such medical devices include, but are not limited to, integrated medical devices that include a combination of a test strip and a lancet, examples of which are described in the aforementioned International Application No. PCT/GB01/05634 (published as WO 02/49507 on Jun. 27, 2002) and U.S. patent application Ser. No. 10/143,399, both of which are fully incorporated herein by reference. One skilled in the art will also recognize that such test strips may have, but are not limited to, an electrochemical or photometric configuration. For illustrative purposes only, medical devices in various figures of the present disclosure were depicted as having an electrochemical configuration.

Moreover, those skilled in the art will appreciate that medical device packages according to embodiments of the present invention can be employed with medical device adapted for the measurement of, for example, glucose, ketones, glycated albumin, coagulation parameters and cholesterol of a sample.

In addition, one skilled in the art will also recognize that medical device packages according to the present invention may be contained within a combined sample collection and metering system designed for in-situ testing. Examples of such systems designed for in-situ testing are disclosed in International Patent Application No. PCT/US01/07169 (published as WO 01/64105 A1 on Sep. 7, 2001) and International Patent Application No. PCT/GB02/03772 (published as WO 03/015627 A1 on Feb. 27, 2003), each of which is fully incorporated herein by reference.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A medical device package comprising:
   a main cap member with a cavity therein, the main cap member including:
      a proximal end; and
      a distal end;
      a medical device comprising a test strip and a dermal tissue penetration member; and
   a minor cap member,
wherein:
   the cavity has a cavity opening at the proximal end of the main cap member; the cavity opening having a size that permits receiving and removably retaining no more than a portion of the medical device with electrical contacts therein such that the electrical contacts project from the cavity opening and minor cap member, and
   the minor cap member is configured to seal the cavity opening once the medical device has been partially received in the cavity.

2. The medical device package of claim 1, wherein the main cap member includes at least one lateral channel and wherein the medical device is securely and removably retained by a friction fit between the medical device and the at least one lateral channel.

3. The medical device package of claim 1, wherein the main cap member includes a directional marker.

4. The medical device package of claim 1, wherein the minor cap member is a breachable minor cap member.

5. The medical device package of claim 1, wherein the minor cap member is configured for permanent attachment to the medical device.

6. The medical device package of claim 1, wherein the main cap member further includes a distal end cavity configured for disabling the medical device.

* * * * *